(12) United States Patent
El-Say et al.

(10) Patent No.: US 10,744,137 B1
(45) Date of Patent: Aug. 18, 2020

(54) LIQUISOLID TABLET CONTAINING COMBINED DOSE OF TADALAFIL AND DAPOXETINE

(71) Applicant: King Abdulaziz University, Jeddah (SA)

(72) Inventors: Khalid M. El-Say, Jeddah (SA); Fayez O. Alotaibi, Jeddah (SA); Nabil A. Alhakamy, Jeddah (SA); Abdelsattar M. Omar, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/734,528

(22) Filed: Jan. 6, 2020

(51) Int. Cl.
*A61K 9/20* (2006.01)
*A61K 31/4985* (2006.01)
*A61K 9/28* (2006.01)
*A61K 31/138* (2006.01)

(52) U.S. Cl.
CPC ........ *A61K 31/4985* (2013.01); *A61K 9/2013* (2013.01); *A61K 9/2027* (2013.01); *A61K 9/2031* (2013.01); *A61K 9/2054* (2013.01); *A61K 9/2813* (2013.01); *A61K 31/138* (2013.01)

(58) Field of Classification Search
CPC .......... A61K 9/14; A61K 9/16; A61K 9/1605; A61K 9/1611; A61K 9/1623; A61K 9/1629; A61K 9/1635; A61K 9/1641; A61K 9/1652; A61K 9/20; A61K 9/204; A61K 9/2009; A61K 9/2013; A61K 9/2018; A61K 9/205
See application file for complete search history.

(56) References Cited

U.S. PATENT DOCUMENTS

| | | | | |
|---|---|---|---|---|
| 5,800,834 | A | * | 9/1998 | Spireas ............... A61K 9/2095 424/451 |
| 2004/0092428 | A1 | * | 5/2004 | Chen .................... A61K 9/1075 424/452 |

FOREIGN PATENT DOCUMENTS

| | | | | |
|---|---|---|---|---|
| EP | 2698145 | | 2/2014 | |
| EP | 3342403 | A1 * | 7/2018 | ........... A61K 31/138 |
| WO | 2014027979 | | 2/2014 | |

OTHER PUBLICATIONS

Dresser et al., "Dapoxetine, a novel treatment for premature ejaculation, does not have pharmacokinetic interactions with phosphodiesterase-5 inhibitors", IJIR (2006) 18, 104-110.
Khames et al., "Investigation of the effect of solubility increase at the main absorption site on bioavailability of BCS class II durg (risperidone) using liquisolid technique", Drug Delivery (2017) 24:1, 328-338.
Lu et al., "Liquisohd technique and its applications in pharmaceutics", Asian Journal of Pharmaceutical Sciences 12 (2017) 115-123.
Lu et al., "Dissolution enhancement of tadalafil by liquisolid technique", Pharm Dev Technol. Feb. 2017; 22(1):77-89.
Shaikh et al., "Design and characterization of orodispersible tablets of Aceclofenac" International Journal of Advances in Pharmaceutical Sciences 1 (2010) 364-368.

* cited by examiner

*Primary Examiner* — Micah Paul Young
(74) *Attorney, Agent, or Firm* — W & C IP

(57) ABSTRACT

A liquisolid tablet formulation, comprising a microcrystalline cellulose carrier; a silica coating; a crosslinked polyvinylpyrrolidone (PVP) superdisintegrant; a solvent comprising polyethylene glycol (PEG) 200 and caprylocaproyl macrogol-8 glycerides; tadalafil; and dapoxetine, wherein the liquid load factor of the formulation is 0.2-0.4 is provided. Methods of making the liquisolid tablet and methods of using the formulation for the treatment of male sexual dysfunction are also provided.

13 Claims, 12 Drawing Sheets

LIQUISOLID TABLET CONTAINING COMBINED DOSE OF TADALAFIL AND DAPOXETINE

FIELD OF THE INVENTION

The invention is generally related to a liquisolid tablet that improves the solubility and enhances the bioavailability of tadalafil and dapoxetine.

BACKGROUND OF THE INVENTION

Male sexual dysfunction (MSD) is a mixed group of complaints that are typically related to a person's inability to respond sexually or to achieve sexual stimulation. Male sexual dysfunction is a common problem mainly associated with erectile dysfunction (ED) and/or premature ejaculation (PE). ED has many causes such as adverse results of using prostate cancer treatment, after exposure to radiotherapy, atherosclerosis problems, as well as those with cardiovascular diseases or diabetes mellitus (Pisansky et al., 2014; Satriyasa, 2017). It was reported that by 2025 ED is expected to affect about 322 million men around the world. The prevalence of PE ranges from 19% to 30% in the general population and is considered the most common sexual dysfunction in men (Gao et al., 2013; Serefoglu et al., 2011). Patient numbers with male sexual dysfunction are expected to double in the next twenty-five years (Ramezani et al., 2015). PE is present in up to 30% of men with ED (Rastrelli et al., 2019). Thus, ED and PE may be considered as an interconnected case of sexual dysfunction.

A potent and selective phosphodiesterase-5 inhibitor (PDE5-I), tadalafil (TDL) is one of the most efficient medicines for the treatment of ED (Andersson, 2018). On the other hand, a selective serotonin reuptake inhibitor (SSRI), dapoxetine (DPX) is has been approved for the treatment of PE (Li et al., 2018; Althof et al., 2010). It is the first oral pharmacological agent used, and the only SSRI approved in more than 60 countries to treat men with PE (Park et al., 2017).

On comparing the on-demand dosing of DPX alone and combined with PDE5-I in subjects with PE and without ED, it was found that a low dose of DPX combined with PDE5-I showed better outcomes compared with that of DPX only. This finding supports the recommendation that the PDE5-Is have a potential role in the treatment of PE without ED (Lee et al., 2013). In addition, the combined use of SSRIs and PDE5-Is provided additive favorable effects in men with PE compared with SSRIs or PDE5-I monotherapy (Bai et al., 2015). Moreover, DPX provided a remarkable treatment benefit in men with PE and comorbid ED on a stable regimen of PDE5-I (Mcmahon et al., 2013). Finally, it was reported that the combination of DPX with TDL is well tolerated and the concomitant administration of TDL and DPX did not affect the pharmacokinetics of both APIs (Dresser et al., 2006).

However, TDL undergoes low bioavailability due to its inherent poor aqueous solubility (Badr-Eldin et al., 2017; Badr-Eldin et al., 2008). Also, DPX suffers from low and variable oral bioavailability that ranges from 15-76% (El-Say et al., 2019). This low and variable drug concentration in the blood may lead to decreased efficacy and/or exaggerated side effects.

To overcome this hurdle that encounters the formulators of the oral solid dosage form, many researchers have developed various approaches to improve drug water-solubility such as the adjustment of the pH, the addition of cosolvent, particle size reduction, solid dispersion (Pandya, 2010), salt formation or formulation of the drug in lipid-based nanovesicles such as liposomes (Sanjay et al., 2013), nanosuspension development (Patel et al., 2011)(Keck and Müller, 2006), prodrug synthesis (Erion et al., 2005), formation of micro- and nano-particles (El-Say and El-Sawy, 2017), or incorporation of drugs into porous structure and nanoemulsion formulations (El-Say et al., 2017)(Ahmed et al., 2018).

However, new formulations that improve the solubility and enhance the bioavailability of tadalafil and dapoxetine are needed.

SUMMARY

An aspect of the disclosure provides a liquisolid tablet formulation, comprising a microcrystalline cellulose carrier; a silica coating; a crosslinked polyvinylpyrrolidone (PVP) superdisintegrant; a solvent comprising polyethylene glycol (PEG) 200 and caprylocaproyl macrogol-8 glycerides; tadalafil; and dapoxetine, wherein the liquid load factor of the formulation is 0.2-0.4. In some embodiments, the liquid load factor is 0.2. In some embodiments, the carrier to coating ratio is 11-13. In some embodiments, the concentration of superdisintegrant is 4-6%. In some embodiments, the ratio of PEG 200 to caprylocaproyl macrogol-8 glycerides is 1:1. In some embodiments, the dose of tadalafil is 2.5-5 mg and the dose of dapoxetine is 15-30 mg.

Another aspect of the disclosure provides a method of preparing a liquisolid tablet formulation, comprising dissolving tadalafil in a solvent comprising PEG 200; dissolving dapoxetine in a solvent comprising caprylocaproyl macrogol-8 glycerides; mixing the dissolved tadalafil and the dissolved dapoxetine to form a combined solution; adding a microcrystalline cellulose carrier, a crosslinked polyvinylpyrrolidone (PVP) superdisintegrant, and silica coating to the combined solution to form a dry mixture; and compressing the dry mixture to form a liquisolid tablet.

Another aspect of the disclosure provides a method of treating male sexual dysfunction in a subject in need thereof, comprising administering a formulation as described herein to the subject.

DETAILED DESCRIPTION

Figure 1A:
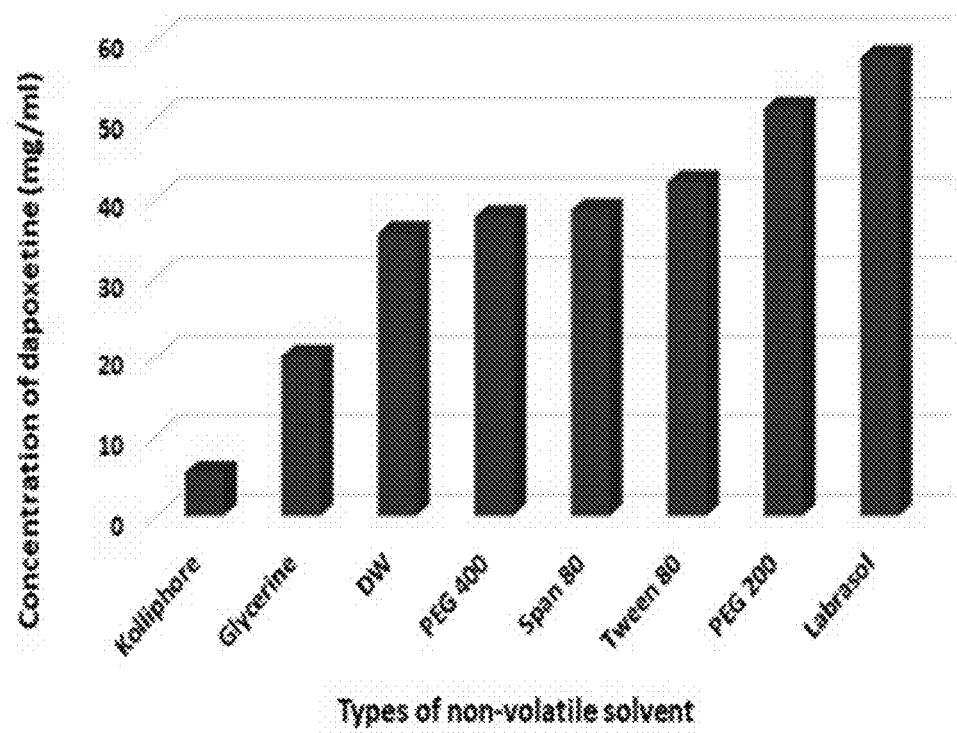
FIG. 1A-B. Solubility of a) DPX and b) TDL in different non-volatile solvents.

Embodiments of the disclosure provide liquisolid tablet formulations that enhance the absorption and thus the bioavailability of both tadalafil and dapoxetine. The formulations described herein are an alternative to currently available marketed oral tablet products comprising each drug.

The liquisolid technique is used to convert a liquid into easily compressible, non-adherent and free-flowing dry powder by mixing excipients comprising a carrier material and a coating material. Liquisolid formulations increase drug release properties and hence the bioavailability of water-insoluble drugs due to the observed increase of the surface area of drug and wetting properties available for dissolution. Liquisolid formulations may also diminish the effect of pH changes on drug release.

Carrier materials should be sufficiently porous to enhance absorption properties and hence absorb liquid sufficiently to enhance the solubility. Suitable carrier materials include but are not limited to a partially depolymerized alphacellulose carrier such as microcrystalline cellulose (e.g. Avicel® PH-101, Avicel® PH-102, Avicel® PH-103, Avicel® PH-105, Avicel® PH-112, Avicel® PH-113, Avicel® PH-200, Avicel® PH-301, and Avicel® PH-302), Dibasic Calcium Phosphate Anhydrous (e.g. Fujicalin®), Magnesium Aluminometasilicate (e.g. Neusilin® US2 and Neusilin® UFL2), cellulose, starch, lactose, and Eudragit® RL and RS.

The coating material should have a high adsorptive property so that the carrier particles can absorb the excessive non volatile solvent layer over the carrier particles and can give a dry solid appearance to the saturated carrier particles having a liquid external layer of non volatile solvent, thus providing dry, non adherent, free flowing powder particles. Suitable coating materials include but are not limited to silica powder (e.g. Aerosil® and Cab-O-Sil® fumed silicas), hydroxy propyl methyl cellulose, Syloid, and titanium dioxide.

In some embodiments, the carrier to coating ratio is 11-13, e.g. about 12.

The formulations described herein may also include superdisintegrants which increase the rate of drug release, its wettability and increases solubility of drug particles within short period of time. Suitable superdisintegrants include but are not limited to a crosslinked polyvinylpyrrolidone (PVP) superdisintegrant (e.g. Polyplasdone XL-10), sodium starch glycolate, crospovidone (e.g. Crospovidone NF), low substituted hydroxypropyl cellulose, and croscarmellose sodium. In some embodiments, the concentration of superdisintegrant is 4-6%, e.g. about 5%.

The tadalafil and dapoxetine therapeutic agents are dissolved in a suitable solvent that is incorporated into the liquisolid formulation. As demonstrated in the Example, polyethylene glycol (PEG) 200 showed the highest solubilization capacity of tadalafil (10.07 mg/ml vs 0.049 mg/ml in distilled water) while Labrasol® showed the highest solubilization capacity of dapoxetine (57.71 mg/ml vs 35.63 mg/ml in distilled water). Upon using a mixture of both solvents, the solubility of both agents was improved and their presence in the molecularly dispersed form (solubilized form) was confirmed. Thus, the disclosure provides a solvent comprising a mixture of PEG 200 and caprylocaproyl macrogol-8 glycerides (i.e. caprylocaproyl macrogol-8/polyoxyl-8 glycerides (Labrasol®)). In some embodiments, the ratio of PEG 200 to caprylocaproyl macrogol-8 glycerides is about 1:1.

In some embodiments, the dose of tadalafil is 2.5-5 mg (e.g. 3-4 mg) and the dose of dapoxetine is 15-30 mg (e.g. 20-25 mg). Exemplary dosage combinations include but are not limited to: 2.5 mg tadalafil and 15 mg dapoxetine, 2.5 mg tadalafil and 30 mg dapoxetine, 5 mg tadalafil and 15 mg dapoxetine, or 5 mg tadalafil and 30 mg dapoxetine.

The liquisolid tablet formulations described herein are useful for delivery of biologically active agents such as tadalafil and dapoxetine to a human or non-human animal subject. In some embodiments, the active agent has a solubility in water (w/v) which is 3% or less, e.g. 1% or less.

The lisquisolid tablet formulations described herein may have a liquid load factor of 0.2-0.4. The liquid load factor is the weight of liquid medication divided by the weight of the carrier material.

Pharmaceutical additives can be added to increase the efficacy or potency of other ingredients in the formulation. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure also provide methods of preparing a liquisolid tablet formulation as described herein. In some embodiments, the method comprises dissolving tadalafil in a solvent comprising PEG 200; dissolving dapoxetine in a solvent comprising caprylocaproyl macrogol-8 glycerides; mixing the dissolved tadalafil and the dissolved dapoxetine to form a combined solution; adding a microcrystalline cellulose carrier, a crosslinked polyvinylpyrrolidone (PVP) superdisintegrant, and silica coating to the combined solution to form a dry mixture; and compressing the dry mixture to form a liquisolid tablet.

In some embodiments, 100 mg of tadalafil is dissolved in the first half of the calculated solvent mixture (PEG 200) and 600 mg of dapoxetine is dissolved in the second half of the solvent mixture (Labrasol®) and the mixture is mixed well. Calculated amounts of Avicel® PH 101, fumed silica, magnesium trisilicate, polyplasdone XL-10, and Methocel® ES are added to the mixture with continuous trituration for 10 min in a mortar and the dried mixture is passed through 20 mesh sieves. Finally, the mixture is mixed with magnesium stearate and talc powder.

The liquisolid tablet formulations of the disclosure are suitable for oral administration. The present disclosure also provides a method of treatment of a human or non-human animal subject by delivery of a substantially insoluble or sparingly soluble biologically active agent, said method comprising administering to said subject liquisolid tablet formulation as described herein.

Embodiments of the disclosure also provide methods of treating male sexual dysfunction in a subject in need thereof, comprising administering a formulation as described herein to the subject. Male sexual dysfunction may include erectile dysfunction and/or premature ejaculation. The subject may be a male or transgender individual.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

It should be understood that throughout the specification the term weight percent (wt %) refers to mass per unit volume, unless otherwise specified.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted, to limit the scope of the invention.

EXAMPLE

Summary

This study aimed to develop an optimized combined-dose liquisolid tablet (LST) containing tadalafil (TDL) and dapoxetine (DPX) with improved bioavailability as a therapy for male sexual dysfunction. A mixture of nonvolatile solvents namely PEG 200 and Labrasol (1:1 w/w ratio) was utilized to prepare fifteen formulations of LSTs that were assessed for their quality characteristics. The solid-state of pure drugs and drugs in LSTs were examined by different techniques. Box-Behnken design (BBD) was employed to statistically explore the effect of the formulation factors on the quality attributes of the LSTs. Mathematical modeling of the dissolution data was carried out by computing the dissolution rate, mean dissolution time, and the dissolution efficiency. Furthermore, an in vivo pharmacokinetic study was carried out for the optimized LST in comparison with the marketed tablets on healthy human volunteers.

The optimized LST revealed acceptable quality limits with enhanced dissolution for both APIs. The pharmacokinetic parameters after oral administration of the optimized LST to human volunteers indicated that the maximum plasma concentration of TDL in LSTs was 122.61 ng/ml within 2 h ($t_{max}$) compared to the marketed tablets which reach to 91.72 ng/ml after 3 h indicating faster onset of action. The AUC was improved for TDL in LST (5231.316 vs 3066.42 ng/ml*h in marketed tablet) and for DPX in LST (1096.416 vs 936.702 ng/ml*h in marketed tablet). The developed combined-dose LST enhanced the oral bioavailability of both APIs due to the improvement of their solubility and then hastening absorption. This enhancement minimizes the associated side effects and improves the treatment of male sexual dysfunction, particularly for diabetic patients.

Materials and Methods

Materials

TDL was gifted from SAJA Pharmaceutical Co. Ltd. (Jeddah, Saudi Arabia). DPX was kindly gifted from Spimaco Addwaeih (Riyadh, Saudi Arabia). Glycerine was supplied by Crescent Diagnostics (Jeddah, Saudi Arabia). Cellulose microcrystalline (Avicel® PH-101), sorbitan monooleate 80 (Span® 80), Macrogolglycerol ricinoleate; Kolliphor® EL (Cremophor® EL), and Polysorbate 80 (Tween® 80) were purchased from Sigma Aldrich (Steinheim, Germany) Silica fumed anhydride, silicon amorphous, silicon dioxide was obtained from Sigma-Aldrich (St. Louis, Mo., USA). Polyethylene glycol (PEG) 200 was purchased from BDH Limited (Poole, England). Polyethylene glycol 400 purchased from Across Organics (NJ, USA). Caprylocaproyl macrogol-8/polyoxyl-8 glycerides (Labrasol®) was supplied by Gattefosse' (Saint-Priest Cedex, France). Crospovidone NF (Polyplasdone XL-10) was supplied by ISP Technologies (Ashland, Ky.). Methanol was purchased from Honeywell (Seelze, Germany) Magnesium stearate was purchased from (Prolabo, France). Magnesium Trisilicate was purchased from Loba Chemie Pvt. Ltd. (Mumbai, India). Talc powder was purchased from Qualigens fine chemicals (Mumbai, India).

Pre Formulation Studies

Solubility Studies

Solubility studies of TDL and DPX were determined in various nonvolatile solvents separately as described previously with full details in the literature (Al-Subaie et al., 2015)(Aldawsari et al., 2018)(El-Say et al., 2019). The solvents used in this study were Span® 80, Tween® 80, PEG 400, PEG 200, Labrasol®, Kolliphor® EL, glycerin and distilled water were used.

Holding Capacity and Determination of the Liquid Load Factor ($L_f$)

The holding capacity for each excipient was obtained by using the previously reported method (El-Say et al., 2019). Different weights (0.5, 1.0, 1.5, 2.0, and 2.5 g) of solvents; PEG 200 and Labrasol; were added to different mortars containing 5 g of Avicel PH-101 and triturated well. Then 0.5 g that gradually increased to 1.0 g of silica was added and triturated to give good distribution for the liquid through the powder blend. Powder addition and trituration was sustained up until mortar contents began to appear as a dry powder. The obtained mixtures were examined for their flowability by determination of angle repose, Hausner ratio and Carr's Index. This procedure was repeated by increasing the weight of silica in the powder to 1.0 g to evaluate if there is an improvement in the flowability of powder blends achieved or not. Finally, the liquid load factor (Lf) which possessed an acceptable flowable and compressible blend, was determined.

Solid-State Characterization Studies

Differential Scanning Calorimetry (DSC)

DSC was carried out to evaluate the thermotropic characteristics and thermal performance of TDL and DPX and the liquisolid compacts using a DSC 8000, PerkinElmer, Inc. (Waltham, Mass., USA). About 5 mg of the sample was sealed in aluminum pans and heated at the rate of 10° C./min, covering a temperature range of 25–400° C. under a nitrogen atmosphere at a flow rate of 100 ml/min.

Fourier Transform Infrared Spectroscopy (FT-IR)

To investigate potential interactions between TDL and DPX with the tablet's excipients in the LST, FT-IR spectra were obtained using a Nicolet iS10, Thermo Scientific Inc., (Waltham, Mass., USA).

Powder X-Ray Diffraction (PXRD)

The crystallinity of liquisolid powder formulations was considered using PXRD. PXRD diffractograms for TDL and DPX and the prepared liquisolid system were determined using the Ultima IV diffractometer (Rigaku Inc., JAPAN).

Formulation of TDL and DPX Liquisolid Tablets

BBD was employed to evaluate the effect of the liquid load factor ($L_f$) as $X_1$, the powder excipient ratio (R) as $X_2$, and the superdisintegrant (Polyplasone XL-10) percentage as $X_3$ on the quality attributes of the LS formulations. Fifteen experimental runs were suggested by the design. $X_1$ was studied in the level from 0.2 to 0.4, $X_2$ from 5 to 15, while $X_3$ from 4 to 6%. Statistical analysis was performed using Statgraphics® Centurion XVII, software (USA) to investigate the effect of these independent variables on the tablet hardness ($Y_1$), the disintegration time ($Y_2$), the dissolution efficiency percent of TDL after 60 min ($Y_3$) and the dissolution efficiency percent of DPX after 60 min ($Y_4$).

Preparation of TDL and DPX Liquisolid Tablets

Fifteen formulations of liquisolid tablets LS-1 to LS-15 were prepared as shown in Table 1. Briefly, 100 mg of TDL was dissolved in the first half of the calculated solvent mixture (PEG 200) and 600 mg of DPX was dissolved in the second half of the solvent mixture (Labrasol®) and the mixture was mixed well. The calculated amounts of Avicel PH 101, fumed silica, magnesium trisilicate, polyplasdone XL-10, and Methocel® ES were added to the mixture with continuous trituration for 10 min in a mortar and the dried mixture were passed through 20 mesh sieves. Finally, the mixture was mixed with magnesium stearate and talc powder. The obtained powder blend of the fifteen formulations was examined for the flowability parameters before their compression into liquisolid tablets with a diameter of 9 mm flat round punches using a single punch tablet machine (Erweka, GmbH, Heusenstamm, Germany).

TABLE 1

Composition of TDL and DPX Liquisolid formulations of 40 tablets per batch based on Box-Behnken design.

| Run # | Avicel, Q | Silica, q | Liquid medication, W Peg 200 | Liquid medication, W Labrasol | TDL | DPX | Methocel 3% | Magnesium trisillicate 5% | Polyplasdone XL-10 | Talc 0.5% | Magnesium stearate 0.5% | Weight of formula | Unit dose weight | Weight of each tablet |
|---|---|---|---|---|---|---|---|---|---|---|---|---|---|---|
| | | | | | | | | (g) | | | | | | |
| LS-1 | 5 | 0.3 | 0.795 | 0.795 | 0.1 | 0.6 | 0.22 | 0.379 | 0.455 | 0.04 | 0.04 | 8.72 | 4.628 | 0.218 |
| LS-2 | 5 | 0.3 | 1.06 | 1.06 | 0.1 | 0.6 | 0.24 | 0.406 | 0.406 | 0.042 | 0.042 | 9.256 | 4.04 | 0.231 |
| LS-3 | 5 | 0.3 | 0.53 | 0.53 | 0.1 | 0.6 | 0.24 | 0.353 | 0.353 | 0.037 | 0.037 | 8.08 | 4.194 | 0.202 |
| LS-4 | 5 | 0.5 | 0.55 | 0.55 | 0.1 | 0.6 | 0.21 | 0.365 | 0.438 | 0.038 | 0.038 | 8.38 | 5.187 | 0.209 |

TABLE 1-continued

Composition of TDL and DPX Liquisolid formulations of 40 tablets per batch based on Box-Behnken design.

| Run # | Avicel, Q | Silica q | Liquid medication, W | | TDL | DPX | Methocel 3% | Magnesium trisillicate 5% | Polyplasdone XL-10 (g) | Talc 0.5% | Magnesium stearate 0.5% | Weight of formula | Unit dose weight | Weight of each tablet |
|---|---|---|---|---|---|---|---|---|---|---|---|---|---|---|
| | | | Peg 200 | Labrasol | | | | | | | | | | |
| LS-5  | 5 | 1.0 | 1.2   | 1.2   | 0.1 | 0.6 | 0.27 | 0.455 | 0.455 | 0.047 | 0.047 | 10.37 | 5.841 | 0.259 |
| LS-6  | 5 | 0.5 | 1.1   | 1.1   | 0.1 | 0.6 | 0.27 | 0.420 | 0.504 | 0.044 | 0.044 | 9.68  | 4.841 | 0.242 |
| LS-7  | 5 | 0.5 | 1.1   | 1.1   | 0.1 | 0.6 | 0.25 | 0.420 | 0.336 | 0.43  | 0.043 | 9.87  | 4.939 | 0.246 |
| LS-8  | 5 | 1.0 | 0.9   | 0.9   | 0.1 | 0.6 | 0.25 | 0.425 | 0.510 | 0.045 | 0.045 | 9.77  | 4.887 | 0.244 |
| LS-9  | 5 | 1.0 | 0.9   | 0.9   | 0.1 | 0.6 | 0.25 | 0.425 | 0.340 | 0.040 | 0.040 | 9.59  | 4.797 | 0.237 |
| LS-10 | 5 | 1.0 | 0.795 | 0.795 | 0.1 | 0.6 | 0.24 | 0.414 | 0.331 | 0.043 | 0.043 | 9.36  | 4.680 | 0.234 |
| LS-11 | 5 | 1.0 | 0.55  | 0.55  | 0.1 | 0.6 | 0.23 | 0.390 | 0.312 | 0.040 | 0.040 | 8.81  | 4.406 | 0.220 |
| LS-12 | 5 | 1.0 | 0.6   | 0.6   | 0.1 | 0.6 | 0.23 | 0.395 | 0.395 | 0.041 | 0.042 | 9.00  | 4.501 | 0.225 |
| LS-13 | 5 | 0.5 | 0.825 | 0.825 | 0.1 | 0.6 | 0.23 | 0.392 | 0.392 | 0.041 | 0.041 | 8.94  | 4.473 | 0.223 |
| LS-14 | 5 | 0.5 | 0.825 | 0.825 | 0.1 | 0.6 | 0.23 | 0.392 | 0.392 | 0.041 | 0.041 | 8.94  | 4.473 | 0.223 |
| LS-15 | 5 | 0.5 | 0.825 | 0.825 | 0.1 | 0.6 | 0.23 | 0.392 | 0.392 | 0.041 | 0.041 | 8.94  | 4.473 | 0.223 |

Pre-Compression Evaluation of the Liquisolid Powder Formulations

Each liquisolid powder blend was evaluated physically before compression into a tablet by determination of the angle of repose (direct method), bulk and tap density, calculation of Hausner ratio and Car's index (compressibility percent) from the following equations 1-3 (Carr, 1965; Hausner, 1967). The angle of repose was determined according to Equation 1.

$$\mathrm{Tan}(\theta) = \left(\frac{2H}{D}\right) \quad \text{(Eq. 1)}$$

While, the Hausner ratio and Carr's index were calculated from equations 2 and 3.

$$\mathrm{Hausner\ Ratio} = \frac{\mathrm{Tapped\ Density}}{\mathrm{Bulk\ Density}} \quad \text{(Eq. 2)}$$

$$\mathrm{Carr's\ Index} = \left(\frac{\mathrm{Tapped\ Density} - \mathrm{Bulk\ Density}}{\mathrm{Tapped\ Density}}\right) \times 100 \quad \text{(Eq. 3)}$$

Post-Compression Evaluation of the Prepared Liquisolid Tablets

The LS tablets were visually inspected for any drawbacks during the compression and then examined for their quality attributes like weight and content uniformity, thickness, hardness, friability, and disintegration time, according to the requirements of the USP Pharmacopeia (The United States Pharmacopeial Convention, 2011).

In-Vitro Disintegration Study

The test was carried out on 6 tablets using a Pharma test disintegration tester according to the USP specifications. Distilled water at 37±0.5° C. was used as a disintegration media and the time in seconds taken for complete disintegration of six tablets was recorded and the average of 6 determinations was reported.

In-Vitro Dissolution Study

The study was performed with the dissolution apparatus II (paddle type). The dissolution medium of 900 ml distilled water at 37±0.5° C. at a rotation of 100 rpm was used. Aliquots of 5 ml were withdrawn at predetermined time intervals 5, 10, 15, 20, 30, 45, and 60 min and filtered through a 0.45 um filter (Millipore Corp., Bedford, Mass., USA). The concentration of TDL and DPX were determined spectrophotometrically at 284 and 291 nm, respectively using a UV-Vis spectrophotometer (Jenway 7315, Bibby scientific Limited, Stone, Staffordshire, UK).

Mathematical Modeling of the Dissolution Data

The data obtained for the in vitro dissolution of TDL and DPX from the fifteen LST formulations and the optimized LST formulation were fitted to different mathematical models to investigate the drug release kinetics and release mechanism. The models used were: Zero (Wagner, 1969), First (Desai et al., 1966), Weibull (Langenbucher, 1972), Hixson-Crowell (Hixson and Crowell, 1931), Higuchi (Higuchi, 1963), Korsmeyer-Peppas (Korsmeyer et al., 1983) and Baker-Lonsdale (Baker and Lonsdale, 1974). The highest value of the coefficient ($R^2$) was used to identify the goodness of fit and the appropriate release model.

Dissolution Rate ($DR_{10}$)

For comparative evaluation, TDL and DPX dissolution rates ($DR_{10}$) for the liquisolid formulations were used (Nokhodchi et al., 2005; Saeedi et al., 2011). The amount of TDL and DPX (in μg) dissolved per min during the first 10 min, was calculated from equation 4

$$DR_{10} = \frac{M \times D}{1000} \quad \text{(Eq. 4)}$$

where M is the total amount of TDL and DPX in each tablet (in this study it is 2500 and 15000 μg for TDL and DPX, respectively) and D designates the percentage of drug dissolved during the first 10 min.

Mean Dissolution Time (MDT)

MDT is defined as the mean residence time of a drug in the formulation (Bernal et al., 2014). It is a beneficial parameter for describing the drug release rate from a dosage form and is calculated using Equation 5:

$$MDT = \frac{\sum_{j=1}^{n} t_j^{AV} \times \Delta Q_j}{\sum_{j=1}^{n} \Delta Q_j} \quad \text{(Eq. 5)}$$

where (j) is the sample number, n is the number of dissolution sample times, ($t_j^{AV}$) is the time at the midpoint between t and t−1 (calculated with (t+t−1)/2), and (ΔQ$_j$) is the additional amount of drug dissolved between t and t−1.
Dissolution Efficiency after 60 Min (DE$_{60}$)

DE$_{60}$% expresses the integrated area under the dissolution curve up to a certain time, t, as a percentage of rectangle area represents 100% dissolution at the same time (Chella et al., 2014)(Ahuja et al., 2007). DE of the formulations was calculated using Equation 6:

$$DE = \frac{\int_0^t Q dt}{Q_{100} \times t} \times 100 \quad \text{(Eq. 6)}$$

where (Q) is the percent of drug released as a function of time, (t) is the total time of drug release, and (Q100) is 100% drug release.

Prediction, Preparation, and Characterization of the Optimized Formulation

Analysis of variance and multiple response optimization developed for responses showed the effect of each input variable and its interaction with other variables was utilized for predicting and obtaining the optimized TDL and DPX liquisolid tablets using Statgraphics software. The optimized formulation was prepared and fully characterized by the hardness, disintegration time and dissolution efficiency after 60 min. This optimized formulation was scaled up to be evaluated in vivo for its pharmacokinetic parameters on human volunteers.

In-Vivo Pharmacokinetic Evaluation on Healthy Human Volunteers

Pharmacokinetic study was carried out for the optimized liquisolid tablet (test) in comparison with the marketed tablet (reference) on healthy human volunteers. The prepared liquisolid tablets and the marketed tablets were administered orally.

Study Design and Conduct

A single-dose one-period parallel design was used in the study. The study was performed in accordance with EMA (European Medicines Agency), ICH (International Conference on Harmonization), GCP (Good Clinical Practice) and FDA (Food and Drug Administration) guidelines. The Protocol was approved by the Egyptian Research and Development Company Research Ethics Committee (ERDC REC) Cairo, Egypt, on its expedited meeting on the 2 Jul. 2018 with the Ethical Approval Code (0569/452). Six subjects (men) per group have participated in this study. Each subject gave written informed consent before participation. The subjects had not donated blood or participated in other drug clinical trials within three months prior to dosing and confirmed abstinence from alcohol, tobacco, grapefruit and caffeinated products throughout the study. The subjects who participated were in good health as determined by past medical history, physical examination, vital signs, and laboratory tests (hematology, biochemistry and urine analysis). They were also screened for hepatitis B and C, and HIV, and remained under close medical supervision until 24 h after the study period. Each subject fasted for at least 12 h before the administration of tablets. Subjects were kept in-house for 72 h prior to and after administration of the drug, so that regular blood sampling could be withdrawn at a predetermined time (as described in the "Blood Sampling" section).

Subjects

Twelve healthy Egyptian male volunteers participated in the study. The age and body mass index (BMI) of the subjects ranged from 21 to 30 years and 20 to 30 kg/m$^2$, respectively with a median height of 172±5.3 cm. Subjects were classified into two groups (6 per group); the first group administered the optimized TDL and DPX liquisolid tablet, and the second group was given the marketed film-coated tablets. The marketed tablets used were TDL 5 mg (Cialis 5 mg, Lilly S. A., Madrid, Spain) and DPX 30 mg (Joypox 30 mg tablets that were produced by SEDICO (South Egypt for Drug Industries Co.) for Inspire Pharmaceutical Co. (IPC Pharma), Cairo, Egypt).

Blood Sampling

A sample of 5 mL of blood was drawn just before and at 0.25, 0.5, 0.75, 1, 1.5, 2, 2.5, 3, 4, 6, 8, 10, 12, 24, 36, 48, 60, and 72 hours after the oral administration of both the test and reference and collected in heparinized tubes. Samples were centrifuged at 3,000 rpm for 5 minutes, and plasma samples were collected and stored at −20° C. until analysis.

Chromatographic Conditions

A high-performance liquid chromatographic method coupled with MS/MS detection (HPLC-MS/MS) was developed, optimized and validated at ERDC laboratories for the determination of TDL and DPX in human plasma (Ahmed, 2018). The method was fully validated according to the "FDA Bioanalytical Method Validation Guidelines 2003". Agilent series 1200, Agilent Technologies, Deutschland GmbH, (Waldbronn, Germany), equipped with G1311A quaternary pump, G1329A, autosampler, G1322A vacuum degasser, and mass hunter software. Chromatography was performed using 75% acetonitrile to 25% of 10 mmoles of ammonium acetate and 100 uL formic acid for each 100 ml water as the mobile phase at a flow rate of 0.3 ml/min and the reverse phase column Intersil ODS −3 (4.6 mm×50 cm, dp Sum Sigma-Aldrich) temporized at 25° C. Sildenafil was used as an internal standard (IS). The retention time was 2.25 and 2.17 minutes for TDL and IS, respectively.

The linearity of the assay for TDL was verified within the concentration range of 1-200 ng/mL with a regression coefficient ($R^2$)=0.998. All the results were within the acceptance criteria as stated in the recommended guidelines. The mean recovery of TDL was 100% at 1 ng/mL (Lower limit of quantification; LLOQ) and 95.3% at 200 ng/mL (Upper limit of quantification; ULOQ). The described method is proved to be sensitive, accurate and reproducible with a lower limit of quantification of 1 ng/mL for TDL.

While the linearity of the assay for DPX was verified within the concentration range of 2-500 ng/mL with a regression coefficient ($R^2$)=0.994. All the results were within the acceptance criteria as stated in the recommended guidelines. The mean recovery of DPX was 99.8% at 2 ng/mL (LLOQ) and 92.2% at 500 ng/mL (ULOQ). The described method is proven to be sensitive, accurate and reproducible with a lower limit of quantification of 5 ng/mL for DPX.

Pharmacokinetic Data Analysis

The plasma concentration of TDL and DPX versus time and the pharmacokinetic parameters were determined by the non-compartmental pharmacokinetic model using PKsolver (An add-in program for pharmacokinetic data). Maximum (peak) plasma concentration over the time span specified ($C_{max}$), and time point of maximum plasma concentration ($T_{max}$), area under the plasma concentration-time curve from zero time to the last measurable concentration ($AUC_{0-t}$) was calculated by the linear trapezoidal method and area under the plasma concentration-time curve from time zero to infinity ($AUC_{0-inf}$) was calculated as the sum of the $AUC_{0-t}$ plus the ratio of the last measurable plasma concentration to the elimination rate constant and the area under the first moment of the plasma concentration-time curve from time zero to infinity ($AUMC_{0-inf}$). Also, the individual estimate of the terminal elimination rate constant (Lambda_z), the mean residence time ($MRT_{0-inf}$) which is calculated by the ratio of AUMC to AUC and elimination half-life ($t_{1/2}$) which was calculated as 0.693/Lambda_z. Moreover, the apparent total body clearance of the drug from plasma after oral administration (Cl/F) was calculated by dividing the dose by AUC and the apparent volume of distribution during the terminal phase after non-intravenous administration (Vz/F) was calculated by multiplying total body clearance by MRT. Finally, the relative bioavailability of the optimized liquisolid tablets (AUC test/AUC standard×100) was determined.

Statistical Analysis

All statistical analyses were performed using GraphPad Prism 8 Software. Two-way ANOVA followed by Sidak's multiple comparisons tests was done to assess the significance among various groups. Results with P<0.05 were considered significant.

Results and Discussion

Pre Formulation Studies

Solubility Study

FIG. 1a illustrates the solubility of TDL in different non-volatile solvents. PEG 200 showed the highest solubilization capacity of TDL (10.07 mg/ml). While the solubility of TDL in distilled water was 0.049 mg/ml which confirms that TDL is practically insoluble in water according to USP which describes the substance that needs more than 10,000 ml to dissolve 1 g with the practically insoluble one.

Figure 1B:
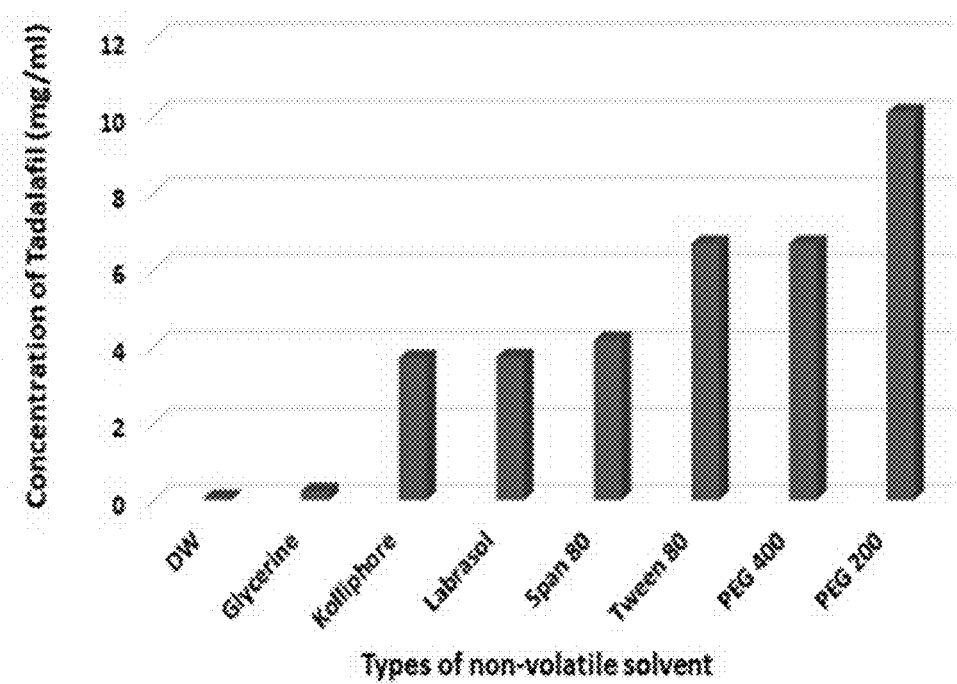

FIG. 1b illustrates the solubility of DPX in different non-volatile solvents. Labrasol® showed the highest solubilization capacity of DPX (57.71 mg/me when compared with other non-volatile solvents in the study. Despite DPX being soluble in water with a solubility value of 35.63 mg/ml, its solubility has been improved markedly with Labrasol® which is favorable in a liquisolid formulation.

Holding Capacity and Determination of Liquid Load Factor ($L_f$)

The flow ability parameters of Avicel® PH 101 after the addition of 0.5 g of silica and after addition of 1 g of silica at different liquid load factor using different weights of the solvent mixture of PEG 200 and Labrasol® (1:1 w/w). The flowability parameters of these blends were evaluated in order to choose the liquid load factor suitable to get acceptable flowability with maximum drug loading in TDL and DPX liquisolid formulations. All the trials showed values of angle of repose more than 43° which indicates the poor flowability of these powder blends. By increasing the amount of the added silica to 1 g, the angle of repose decreased to be 37° which confirms the improvement of the flowability of the powder blends. The same finding has been displayed with the results of Hausner ratio and Carr's index of the same powder blends as the Hausner ratio values ranged from 1.18 to 1.25 and the Carr's index from 15 to 20, respectively which revealed that the addition of 1 g silica to the powder blends was of a great value in the improvement of the flowability. This finding could be explained by the addition of nanometer-sized silica to reduce the van der Waals interparticle attractive force between the powder particles which subsequently improve their bulk flow behavior (Staniforth and Aulton, 2007). Also, this result can be explained by the ability of silica powder to spread on the surface of the other excipient and prevent them from contacting directly (Zimmermann et al., 2004). Moreover, a nanometer-sized flow regulating particles such as silica wedged in between two micrometer-sized host particles forming an equilateral triangle lattice structure and reduced the van der Waals attractive force between the host particles dramatically (Meyer and Zimmermann, 2004).

Solid-State Characterization Studies

Differential Scanning Calorimetry (DSC)

Figure 2A:
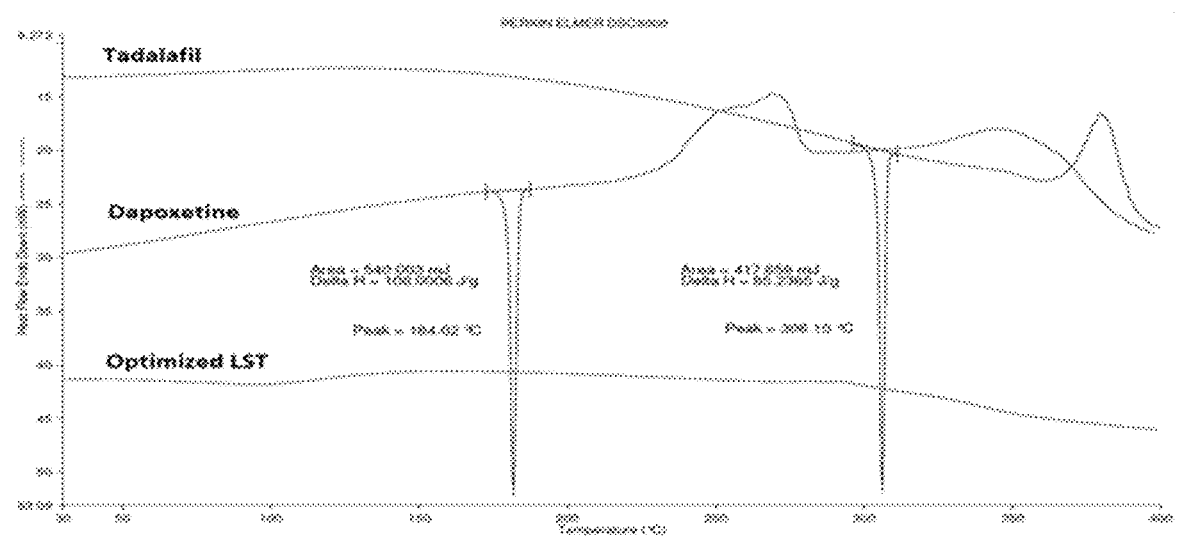
FIG. 2A-C. Solid-state characterization by a) DSC Thermogram, b) FTIR spectra, and c) PXRD diffractograms of tadalafil, dapoxetine, and optimized liquisolid tablet.

FIG. 2a showed the DSC thermograms of raw TDL, raw DPX and the optimized liquisolid formulation. The obtained thermograms showed an endothermic peak around their melting point. In the thermogram of TDL, a sharp endothermic peak corresponding to the melting point of TDL appears at 306.10° C. which indicates the crystalline nature of TDL. The thermogram of DPX showed a sharp endothermic peak corresponding to its melting point at 184.02° C. indicating the crystalline nature of DPX Whereas no peak was obtained in the DSC thermogram of the optimized liquisolid tablet suggesting that the drugs are in a completely solubilized state in the liquisolid system. This observation could be due to the formation of a solid solution in the liquisolid powder form which means that the drugs are dispersed in the liquisolid matrix at the molecular level (Hu et al., 2012). The absence of the endothermic peak can also be attributed to the suppression of thermal feature of the drug because of the formation of an amorphous solid solution (El-Sayyad et al., 2017).

Flourier Transform Infra-Red Spectroscopy (FT-IR)

Figure 2B:
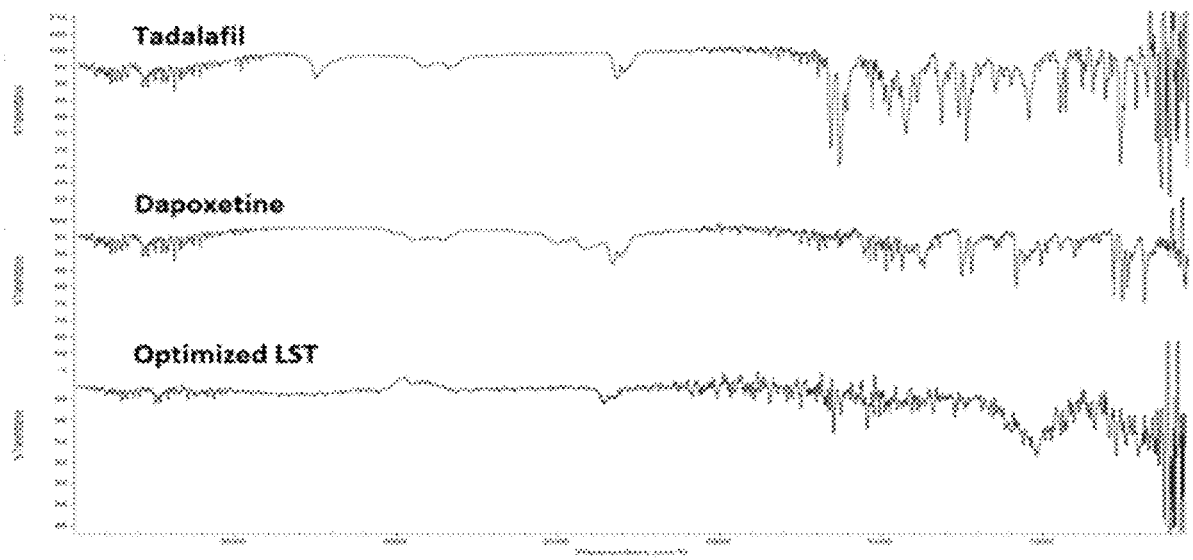

FIG. 2b showed FT-IR spectra of raw TDL, raw DPX and the liquisolid formulation. Absorption peaks properties for TDL were recorded in the 1800-525 $cm^{-1}$ range. This spectral range contains 1720 to 1150 $cm^{-1}$ domains, important for the finding of TDL analogue. The specific TDL absorption bands of the FTIR spectrum were recorded at 1675 cm-1 (properties of amides C=O), 1646 $cm^{-1}$ (C=C aromatic). The band of 1435 $cm^{-1}$ relates to the stretching vibration C-N, and the band 746 $cm^{-1}$ is representative of benzene (Mateescu et al., 2017). Also, it can be recognized from FIG. 2b which shows the characteristic DPX peaks of 4000, 3,053, 2,400, 1,500, and 1,100. The IR spectrum of Labrasol® showed broadband at 2,850 $cm^{-1}$ indicating the presence of a hydroxyl group. In addition, the presence of a carbonyl group was confirmed by the appearance of a characteristic band at 1,100 $cm^{-1}$. The shift of both the hydroxyl and carbonyl groups can be attributed to hydrogen bonding. The absorption bands of the optimized liquisolid formulation did not show interference with the characteristic drugs peaks, indicating the absence of chemical interaction between TDL or DPX with liquisolid formulation excipients and entrapment of drugs inside the carrier matrix of the formulation (Abourehab et al., 2018; Sanka et al., 2014).

Powder X-ray diffraction (PXRD)

Figure 2C:
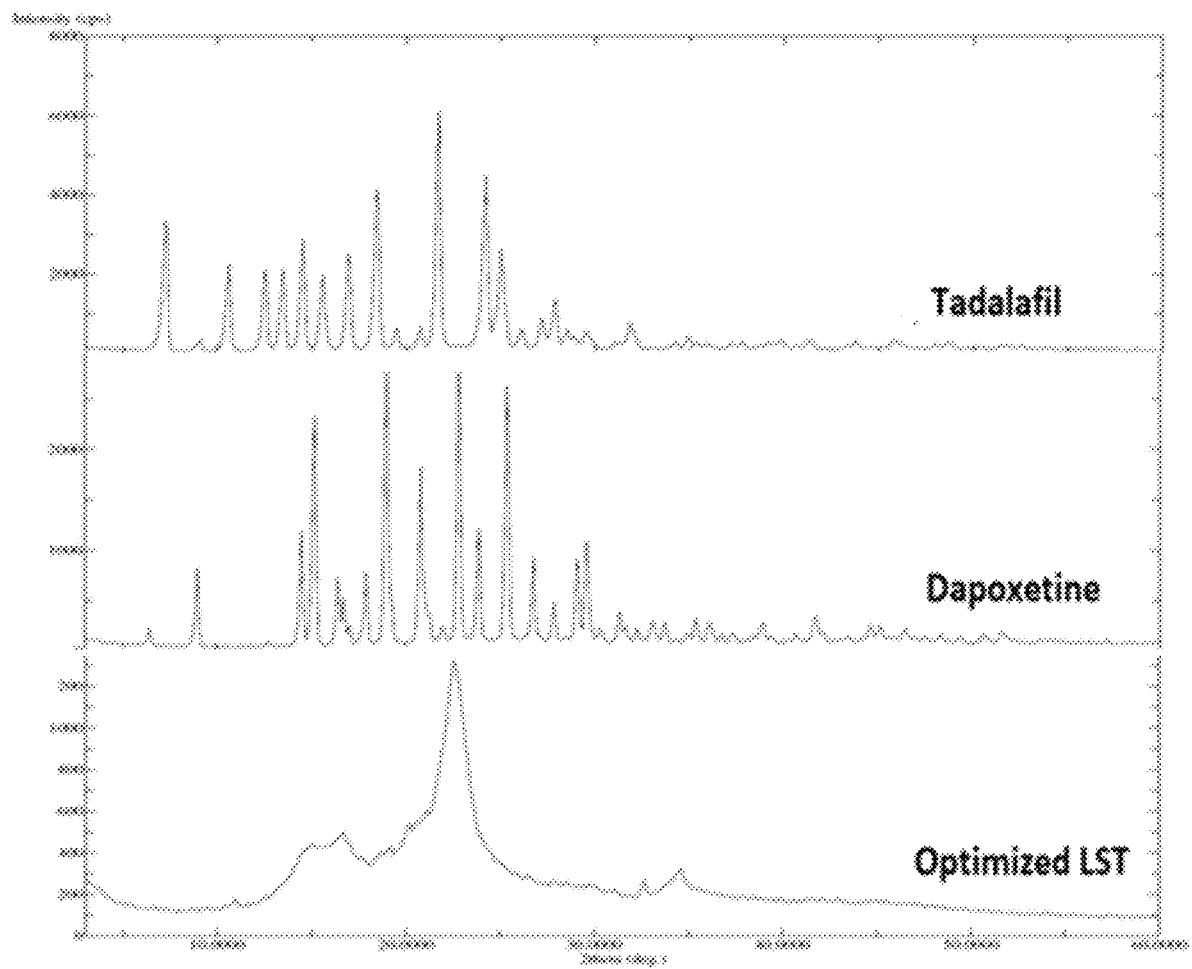

PXRD is used to determine the crystalline state of drugs in pure state and in liquisolid formulation. It measures the disappearance of constructive specific peaks of drugs in the liquisolid formulation and retaining peaks of the carrier material. The PXRD pattern in FIG. 2c of the pure drug (TDL) showed sharp diffraction peaks at 7, 10.5, 11.5, 12.45 and 22° with high intensity which indicates that the pure drug is present in the crystalline state. The PXRD in FIG. 2c demonstrated that pure DPX was clearly in the crystalline state as it showed sharp distinct peaks at 20 diffraction angles of 9, 15, 18, 21, 23 and 25.5° with high intensity which indicated that the pure drug is in the crystalline state. The decrease in the number and intensity of characteristic peaks in the XRD pattern of the liquisolid formulation as illustrated in FIG. 2c indicated the conversion of both drugs from crystalline to amorphous form. This lack of crystallinity in the formulation might be due to the solubilization of drugs in non-volatile liquid vehicles and subsequent adsorption on Avicel® and fumed silica. The solubilization or amorphization of the drug in the liquisolid technique leads to the resulting improvement in the apparent solubility and the dissolution rate of the drug as reported before (Key et al. 2018).

Formulation of the Liquisolid Tablets

Fifteen formulations of the liquisolid powder blends were prepared as suggested by BBD (Table 1). All formulations were evaluated before compression for their flow and packing properties and after compression for their quality attributes of the prepared liquisolid tablets as discussed in the following sections.

Evaluation of the Liquisolid Tablets

Pre-Compression Evaluation

The micromeritic properties of the pre-compressed liquisolid powder blends such as Hausner's ratio, Carr's index, and angle of repose were found to be in the range of 1.09-1.31, 5.1-25 and 21-41°, respectively which indicate that, the acceptable flow properties of the powder blends for all formulations. It was obvious from the data in Table 2 that two formulations (LS-11 and LS-15) out of 15 LS formulations had passable flow property because they have highest values of Hausner ratio, Carr's index and angle of repose (1.31, 25 and 41° for LS-11 and LS-15) whereas LS-8, LS-9, LS-12 formulations had fair flow. On the other hand, the rest of the remaining formulations exhibited good to excellent flow behavior as the value of the Hausner ratio was less than 1.2 (Hausner, 1967). Also, these formulations can be compressed as Carr's index data showed results less than 21% (Staniforth and Aulton, 2007) and the angle of repose was less than 35.

strength of the prepared LSTs as well as overcome the poor compressibility of the liquisolid powders. The good results of the tablet hardness may be due to hydrogen bonding between Avicel® molecules and PEG 200 (Javadzadeh et al., 2008). Regarding the in vitro disintegration time for each batch of LSTs, it was found that the mean of the disintegration times for all investigated tablets was less than 10 minutes, which met the Pharmacopoeial requirements. The disintegration time of the prepared tablets was ranged 0.26 min for LS-4 to 6.29 min for LS-9 that showed the longest disintegration time.

In-Vitro Dissolution Studies

Figure 3B:
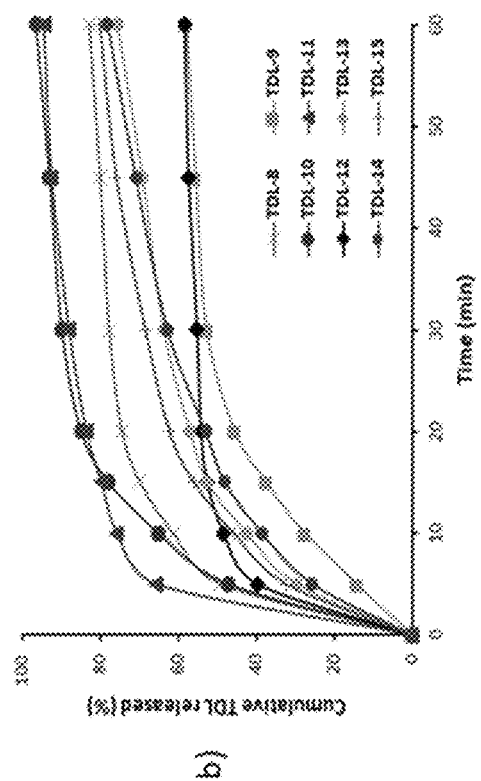
FIG. 3A-D. In vitro release profiles of TDL and DPX from different liquisolid formulations (A-D).
Figure 3A:
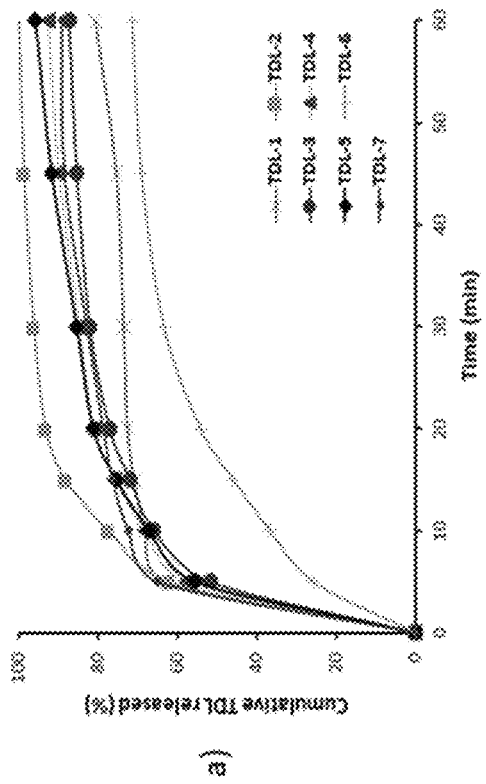
Figure 3D:
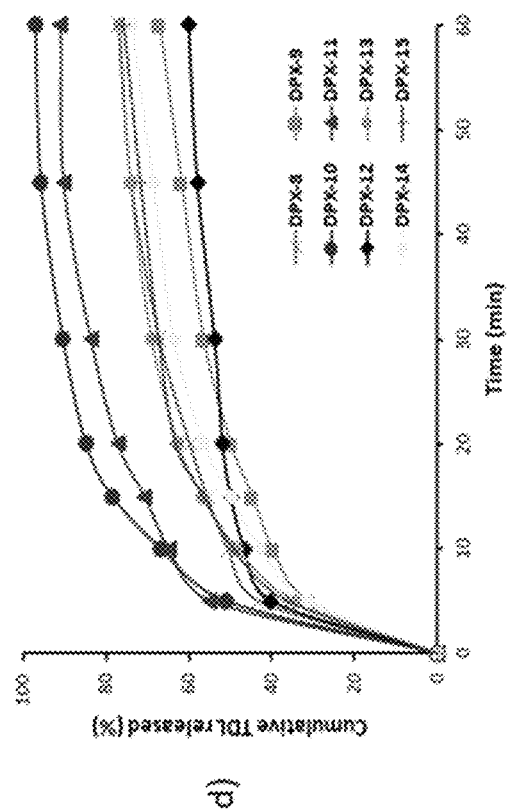
Figure 3C:
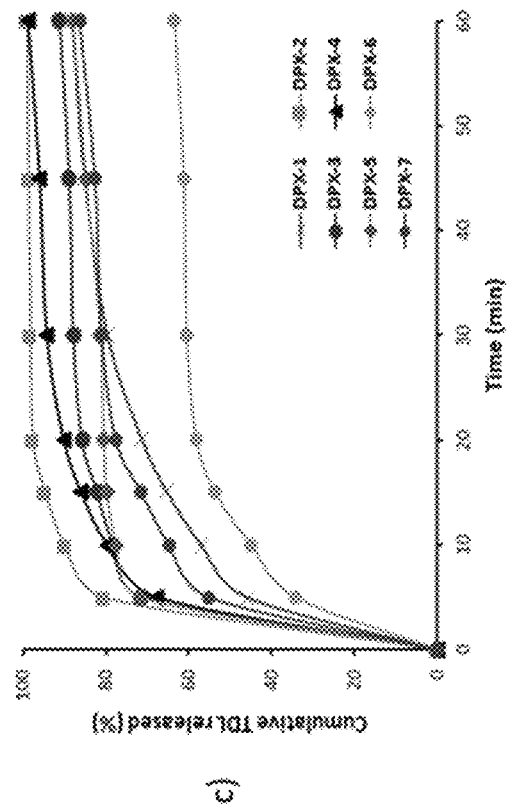
Figure 4B:
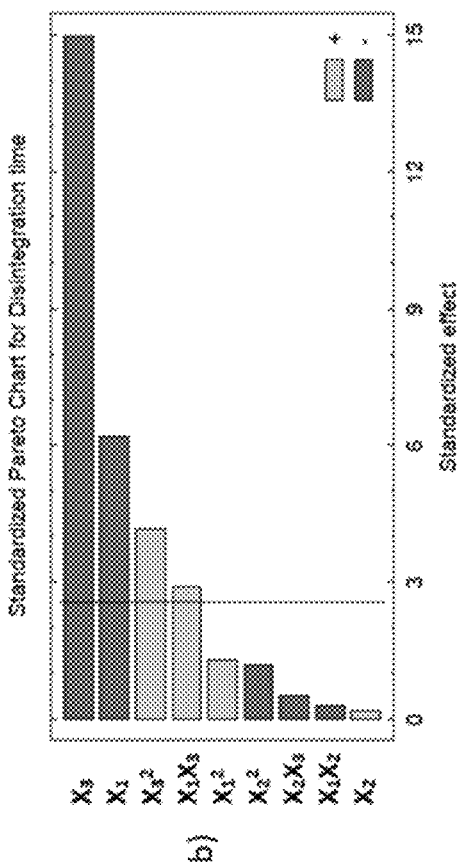
FIG. 4A-D. Pareto charts for all the studied responses ($Y_1$-$Y_4$) A) hardness, B) disintegration time, C) DE of TDL, and D) DE of DPX.
Figure 4A:
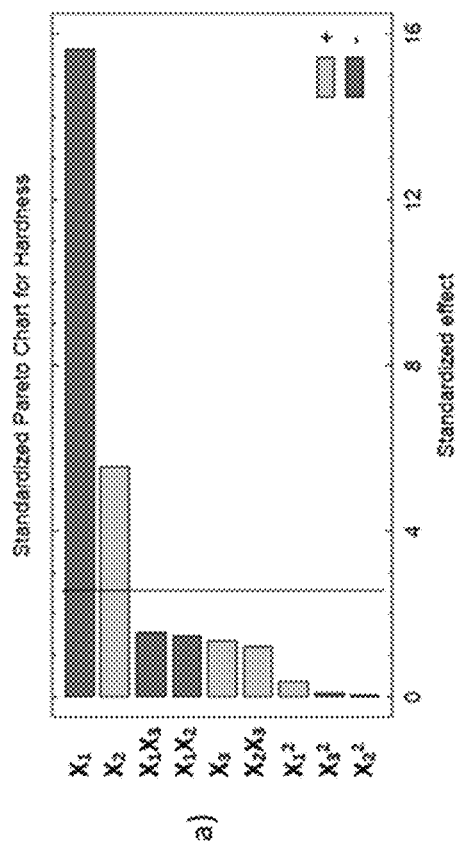
Figure 4D:
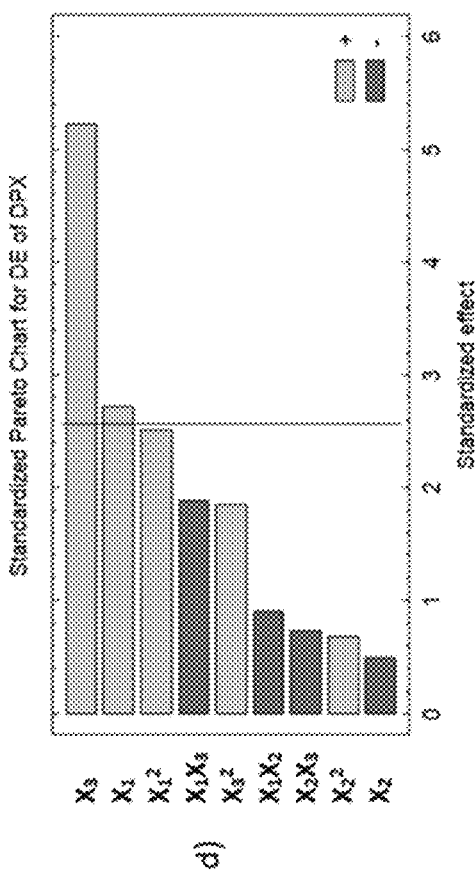
Figure 4C:
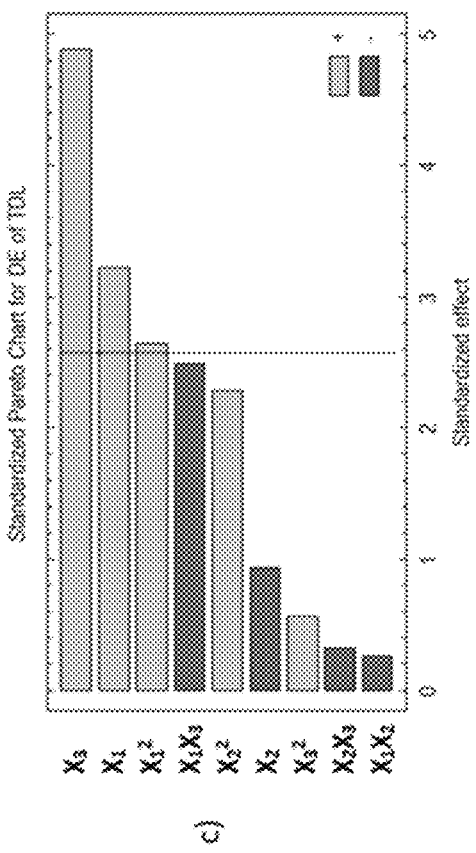

In-vitro dissolution profiles of the fifteen formulations of LSTs were presented in FIGS. 3a&b and FIGS. 3c&d for TDL and DPX, respectively. It was found that, among the fifteen formulations for TDL, LS-2 has maximum dissolution rate that released 75% of its drug content in the first 10 min and 100% in 60 min followed by LS-11 and LS-7 which released 75.76 and 72.45% during the first 10 min respectively and more than 89% after 60 min for both formulations. Most of the prepared formulations released more than 75% of their TDL within 60 min except formula LS-6, LS-9, and LS-12 which released 57.84, 71.45 and 58.34%, respectively within 60 min. Also, LS-2 released more than 80% of its DPX content in the first 10 min and 98.8% in 60 min followed by LS-4 and LS-3 which released 85.97 and 82.20% during the first 10 min and more than 90% during the study period of time. Most of the prepared liquisolid tablets released more than 75% of their DPX within 60 min

TABLE 2

Pre-compression and post-compression properties of liquisolid formulations.

| | Pre-compression properties | | | | Post-compression properties | | | | | |
|---|---|---|---|---|---|---|---|---|---|---|
| | Hausner ratio | Carr's index | Angle of repose | Type of flow | Friability (%) | Hardness (N) | Weight (mg) | Disintegration time (mm) | Content of TDL % | Content of DPX % |
| LS-1 | 1.1 | 14.5 | 29 | Excellent | 0.461 | 58.02 | 200 | 2.54 | 95.2 | 95.8 |
| LS-2 | 1.2 | 19.7 | 26 | Good | 0.151 | 38.91 | 227 | 0.78 | 95.9 | 97.6 |
| LS-3 | 1.09 | 8.78 | 21 | Excellent | 0.357 | 56.44 | 199 | 1.04 | 99.6 | 99.8 |
| LS-4 | 1.1 | 5.1 | 26 | Excellent | 0.356 | 35.28 | 207 | 0.26 | 101.1 | 99.9 |
| LS-5 | 1.1 | 10 | 30 | Excellent | 0.334 | 47.14 | 259 | 0.57 | 97.3 | 98.2 |
| LS-6 | 1.2 | 12 | 35 | Good | 0.300 | 41.85 | 239 | 3.86 | 97.8 | 100.1 |
| LS-7 | 1.18 | 15.4 | 30 | Excellent | 0.294 | 36.75 | 235 | 1.13 | 102.2 | 99.3 |
| LS-8 | 1.19 | 16 | 34 | Fair | 0.253 | 48.51 | 244 | 2.32 | 97.1 | 100.1 |
| LS-9 | 1.21 | 17.5 | 36 | Fair | 0.245 | 49.69 | 238 | 6.29 | 99.0 | 97.3 |
| LS-10 | 1.15 | 13.4 | 31 | Good | 0.268 | 33.81 | 234 | 3.46 | 103.2 | 95.6 |
| LS-11 | 1.31 | 25 | 41 | Passable | 0.219 | 32.14 | 220 | 1.12 | 95.6 | 95.5 |
| LS-12 | 1.2 | 20 | 34 | Fair | 0.193 | 45.96 | 226 | 4.02 | 98.8 | 98.6 |
| LS-13 | 1.17 | 14 | 34 | Good | 0.170 | 44.2 | 223 | 1.86 | 101.3 | 102.2 |
| LS-14 | 1.14 | 12.5 | 31 | Good | 0.164 | 43.81 | 237 | 1.62 | 102.1 | 99.9 |
| LS-15 | 1.3 | 25 | 41 | Passable | 0.086 | 42.63 | 222 | 1.79 | 100.1 | 99.6 |

Post-Compression Evaluation

Quality control tests of the prepared LSTs presented in Table 2 revealed that the TDL content of all formulations was found to be in the range of 95.2% to 100.3% in LS-1 and LS-10, respectively while DPX content of all formulations was in the range of 95.5% to 102.2% for LS-10 and LS-13, respectively. These results were compiled with the official specifications of USP and reflect the uniformity of weight in all formulations (The United States Pharmacopeia, 2005). Also, there is no observed variation in the thickness of all formulations. The friability and the hardness of all tablet formulations ranged from 0.086-0.461%, and 32.14-58.02 N, respectively which complied with BP friability test limits (<1%). The friability and hardness results reflected the acceptable mechanical properties and good breaking except formula LS-6, LS-9, LS-12 and LS-14 which released 63, 67, 60 and 73.8%, respectively. Results illustrated that there is a relationship between the superdisintegrant and the dissolution profile. Formulations containing a high percentage of superdisintegrant (LS-2), showed the highest cumulative amount of TDL and DPX released. In contrast, the formulations containing a low percentage of superdisintegrant (LS-9 and LS-12) showed the lowest cumulative amount of TDL and DPX released. This result might be attributed to the short disintegration time of liquisolid tablets led to the rapid dissolving of the tablet into small particles thus increasing the surface area exposed to the medium and enhancing the dissolution and bioavailability of the drug and vice versa (Patel et al., 2015).

Kinetic Treatment of the Release Data According to Mathematical Models

According to the $R^2$ values, kinetic analysis of the in vitro release data of the prepared formulations was found to follow the Weibull model. Pharmaceutical systems comply with this model when they demonstrate a linear plot when the logarithm of the amount of drug released is plotted versus the logarithm of time (Sousa Lobo and Costa, 2001). The computed β values for these formulations were greater than 1. The β value was used to identify the release mechanism since there is a linear relationship between these values of β and the values of the exponent (n-values) used in the Korsmeyer-Peppas model (Papadopoulou et al., 2006). Unlike the n exponent which is valid only for the first 60% of release, this value can be successfully applied to almost all kinds of dissolution/release curves (Sousa Lobo and Costa, 2001).

The dissolution rate after the first 10 min ($DR_{10}$) was taken as a measure of the extent and the rate of drug dissolved from the prepared formulations. The results in the tables clearly affirm that the liquisolid formulations LS-2, LS-11 and LS-7 showed the highest value of $DR_{10}$ with 193.25, 189.42 and 181.15 µg/min, respectively of its TDL content during the first 10 min. Whereas the formulations LS-2, LS-4, and LS-3 showed the highest values of $D_{R10}$ with 1349.79, 1195.44, and 1174.67 µg/min, respectively of its DPX content during the first 10 min.

Also, the calculated values of both dissolution efficiency after 60 min ($DE_{60}$%) and the mean dissolution time (MDT) for the liquisolid formulations were reported in Tables 3 and 4 for TDL and DPX, respectively. In addition, the MDT value of TDL ranged from 6.9 h in LS-12 to 16.57 h in LS-14. Whereas, the value of MDT was increased from 4.39 h in LS-2 to 13.98 h in LS-9 which could be ordered as a function of the solubility of the drug. $DE_{60}$ values in both drugs increased with an increase in $DR_{10}$ and this is indicated that the liquisolid approach was markedly enhanced the dissolution rate and efficiency.

TABLE 3

Box-Behnken design matrix of LSTs showing the independent and dependent variables.

| | Independent variables | | | Dependent variables | | | |
|---|---|---|---|---|---|---|---|
| Run # | $X_1$ | $X_2$ | $X_3$ | $Y_1$ | $Y_2$ | $Y_3$ | $Y_4$ |
| LS-1 | 0.2 | 15.0 | 5.0 | 58.02 | 2.54 | 70.285 | 71.858 |
| LS-2 | 0.3 | 5.0 | 6.0 | 38.91 | 0.78 | 87.871 | 91.812 |
| LS-3 | 0.2 | 10.0 | 6.0 | 56.44 | 1.04 | 74.851 | 82.016 |
| LS-4 | 0.4 | 10.0 | 6.0 | 35.28 | 0.26 | 78.682 | 86.741 |
| LS-5 | 0.3 | 15.0 | 6.0 | 47.14 | 0.57 | 79.418 | 78.323 |
| LS-6 | 0.3 | 5.0 | 4.0 | 41.85 | 3.86 | 55.255 | 54.192 |
| LS-7 | 0.4 | 15.0 | 5.0 | 36.75 | 1.13 | 78.256 | 74.047 |
| LS-8 | 0.2 | 5.0 | 5.0 | 48.51 | 2.32 | 70.918 | 62.051 |
| LS-9 | 0.2 | 10.0 | 4.0 | 49.69 | 6.29 | 44.375 | 51.427 |
| LS-10 | 0.4 | 10.0 | 4.0 | 33.81 | 3.46 | 80.555 | 81.886 |
| LS-11 | 0.4 | 5.0 | 5.0 | 32.14 | 1.12 | 82.183 | 76.889 |
| LS-12 | 0.3 | 15.0 | 4.0 | 45.96 | 4.02 | 51.630 | 51.115 |
| LS-13 | 0.3 | 10.0 | 5.0 | 44.20 | 1.86 | 57.564 | 61.947 |
| LS-14 | 0.3 | 10.0 | 5.0 | 43.81 | 1.62 | 56.571 | 57.015 |
| LS-15 | 0.3 | 10.0 | 5.0 | 42.63 | 1.79 | 62.234 | 61.171 |

Response Surface Methodology for Optimization of the Formulation

RSM has been widely used in formulations development of modern products and for the modification of existing products. It produces polynomial equations and maps the responses over formulation variables to determine the optimum formulation (Bushra et al., 2014). This study is based on RSM to recognize the influence of dependent variables ($X_1$, $X_2$, and $X_3$) on different response variables ($Y_1$, $Y_2$, $Y_3$, and $Y_4$). Table 3 listed the BBD matrix that involves the independent and dependent variables of all suggested formulations.

Effect of the Independent Variables on the Tablet Hardness ($Y_1$)

Hardness is a crucial test for evaluating the mechanical durability of LSTs. Table 3 showed the variabilities in the hardness of the prepared LSTs that ranged from 32.14 to 58.01 N for LS-11 and LS-1, respectively on changing the levels of the investigated factors. The estimated effects of the investigated factors and associated p values on the responses were displayed in Table 4 and standardized Pareto chart in FIG. 4. ANOVA results exposed a significant antagonist effect of the liquid load factor ($X_1$) on the hardness ($Y_1$) with a p-value of 0.0001. While the excipient ratio ($X_2$) was found to have a significant synergistic effect on $Y_1$ with a p-value of 0.0026 as presented in Table 4 and FIG. 4. The prediction equation (7) to correlate individual and significant variables with the obtained hardness is shown below:

$$\text{Hardness}(Y_1) = 45.258 - 22.3X_1 + 0.379X_2 + 3.366X_3 + 32.417X_1^2 - 2.45X_1X_2 - 13.2\ X_1X_3 - 0.0006X_2^2 + 0.206X_2X_3 - 0.066X_3^2 \quad \text{(Eq. 7)}$$

TABLE 4

Statistical analysis of variance (ANOVA) of the responses ($Y_1$-$Y_4$) results.

| | Hardness ($Y_1$) | | Disintegration time ($Y_2$), min | | Dissolution efficiency for TDL ($Y_3$), % | | Dissolution efficiency for DPX ($Y_4$), % | |
|---|---|---|---|---|---|---|---|---|
| Factors | Estimate | P-Value | Estimate | P-Value | Estimate | P-Value | Estimate | P-Value |
| $X_1$ | −18.671 | 0.0001* | −1.555 | 0.0016* | 14.791 | 0.0233* | 13.020 | 0.0417* |
| $X_2$ | 6.615 | 0.0026* | 0.045 | 0.8643 | −4.302 | 0.3913 | −2.420 | 0.6344 |
| $X_3$ | 1.615 | 0.2337 | −3.745 | 0.0001* | 22.415 | 0.0045* | 25.009 | 0.0034* |
| $X_1^2$ | 0.648 | 0.7271 | 0.476 | 0.2529 | 17.814 | 0.0460* | 17.711 | 0.0535 |
| $X_1X_2$ | −2.451 | 0.2061 | −0.105 | 0.7786 | −1.647 | 0.8096 | −6.158 | 0.4044 |
| $X_1X_3$ | −2.641 | 0.1783 | 1.025 | 0.0339* | −16.133 | 0.0553 | −12.721 | 0.1188 |
| $X_2^2$ | −0.031 | 0.9863 | −0.434 | 0.2915 | 15.427 | 0.0710 | 4.788 | 0.5267 |
| $X_2X_3$ | 2.061 | 0.2764 | −0.185 | 0.6234 | −2.128 | 0.7560 | −4.991 | 0.4939 |
| $X_3^2$ | −0.131 | 0.9431 | 1.536 | 0.0087* | 3.794 | 0.5983 | 13.042 | 0.1232 |

TABLE 4-continued

Statistical analysis of variance (ANOVA) of the responses ($Y_1$-$Y_4$) results.

| Factors | Hardness ($Y_1$) | | Disintegration time ($Y_2$), min | | Dissolution efficiency for TDL ($Y_3$), % | | Dissolution efficiency for DPX ($Y_4$), % | |
|---|---|---|---|---|---|---|---|---|
| | Estimate | P-Value | Estimate | P-Value | Estimate | P-Value | Estimate | P-Value |
| $R^2$ | 98.269 | | 98.318 | | 91.366 | | 90.764 | |
| Adj. $R^2$ | 95.152 | | 95.290 | | 75.825 | | 74.139 | |

Note:
*Significant effect of factors on individual responses.
Abbreviations:
$X_1$, liquid load factor;
$X_2$, excipient ratio;
$X_3$, superdisintegrant concentration;
$X_1X_2$, $X_1X_3$, $X_2X_3$, the interaction term between the factors;
$X_1^2$, $X_2^2$, and $X_3^2$ are the quadratic terms of the factors;
$R^2$, R-squared; and
Adj-$R^2$, Adjusted R-squared.

Figure 5B:
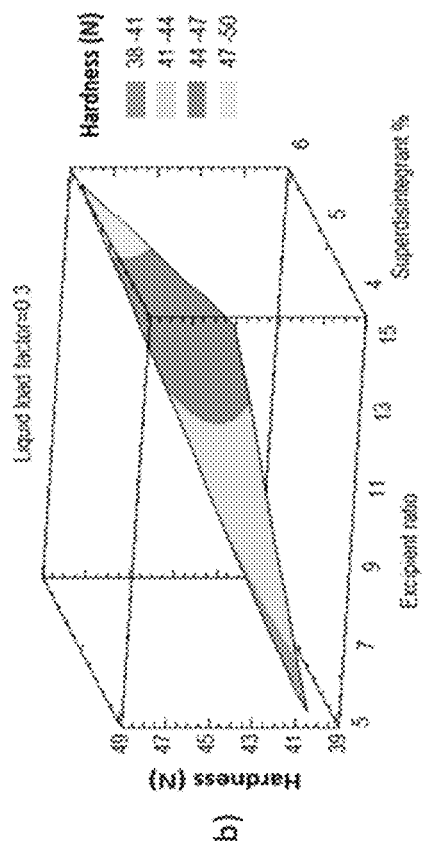
FIG. 5A-D. Response surface plots showing the effect of the independent variables on $Y_1$ and $Y_2$ (A-D).
Figure 5A:
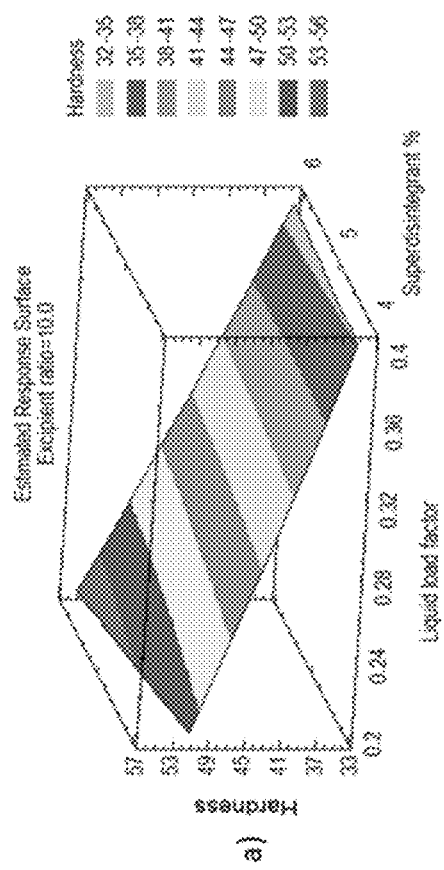

FIG. 5a revealed that there is an inverse relationship between the liquid load factor ($X_1$) and the hardness ($Y_1$) of the formulations. As the $X_1$ increases from 0.2 to 0.4 at the same level of the other factors, the hardness decreased from 58.01 to 36.75 N in LS-1 and LS-7, respectively and from 56.44 to 35.28 N in LS-3 and LS-4, respectively. This trend can be confirmed by the decrease in the hardness from 48.51 to 32.14 in LS-8 and LS-11, respectively as $X_1$ increased from 0.2 to 0.4.

On the other hand, FIG. 5b revealed that increasing the excipient ratio percentage ($X_2$) in the LSTs showed a significant increase in tablet hardness. The increase in $X_2$ from 5 to 15 always accompanied by an increase in the hardness of tablets. At the same level of both $X_1$ and $X_3$ and increasing the $X_2$ from 5 to 15, the hardness increased from 38.91 to 47.14 N in LS-2 and LS-5, respectively and from 41.85 to 45.96 N in LS-6 and LS-12, respectively. This observation could be confirmed by the increase of $Y_1$ from 48.51 to 58.04 N for LS-8 and LS-1, respectively. This may be attributed to the formation of hydrogen bonding between hydrogen atoms on the adjacent cellulose molecules in Avicel® PH-101 that revealed by DSC, FTIR, and XRD investigation. In addition, PEG 200 molecules contain more hydroxyl groups, thus there is also a probability of forming hydrogen bonds with Avicel® PH 101 (Patel et al., 2015).

Effect of the Independent Variables on Tablet Disintegration ($Y_2$)

Fast disintegration of tablets is necessary to ensure the tablets' rapid break down into smaller fragments to yield the largest possible surface area available for dissolution media (Elkordy et al., 2013). The disintegration time of all LSTs ($Y_2$) was in the range from 0.26 to 6.29 min for LS-4 and LS-9, respectively as showed in Table 3.

Figure 5D:
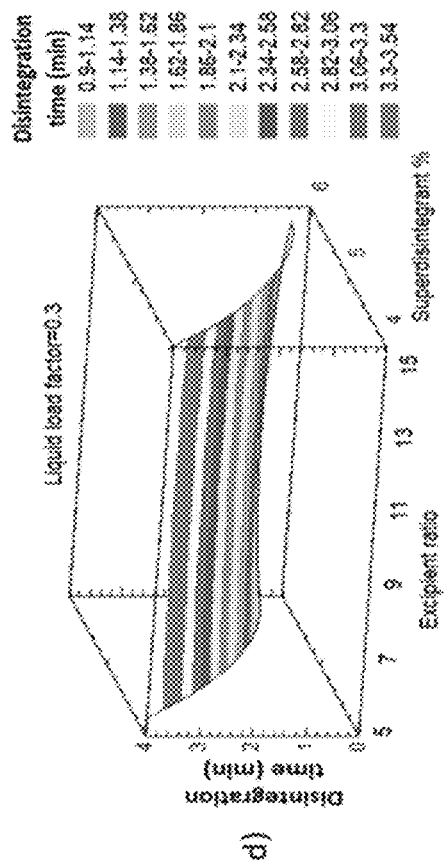

FIG. 5d revealed that there is an inverse relationship between the pattern of disintegration time ($Y_2$) and superdisintegrant concentration ($X_3$), i.e. when the $X_3$ increases, the disintegration time decreases. As the $X_3$ increases from 4 to 6% at the same level of the other factors, the disintegration time decreased from 4.02 to 0.57 min in LS-12 and LS-5, respectively and from 3.86 to 0.78 min in LS-6 and LS-2, respectively. This trend can be confirmed by the decrease in the disintegration time from 3.46 to 0.26 min in LS-10 and LS-4, respectively as $X_3$ increased. This finding due to the rapid water-absorbing nature, as well as the capillary and swelling mechanisms of polyplasdone that build up the pressure internally leading to faster disintegration (Kornblum and Stoopak, 1973). Also, polyplasdone polymers are closely cross-linked homopolymers of polyvinyl pyrrolidones with porous particle structure that allows them to quickly absorb liquids into the tablet by capillary action and to produce rapid volume enlargement and hydrostatic pressures that result in tablet disintegration. It was reported that polyplasdone has non-ionic structure which prevent its binding to ionic drug moieties. Moreover, polyplasdone does not form a gel at higher concentrations and for this reason it is also used to enhance the solubility of drugs and improve their dissolution (Yen et al., 1997).

Figure 5C:
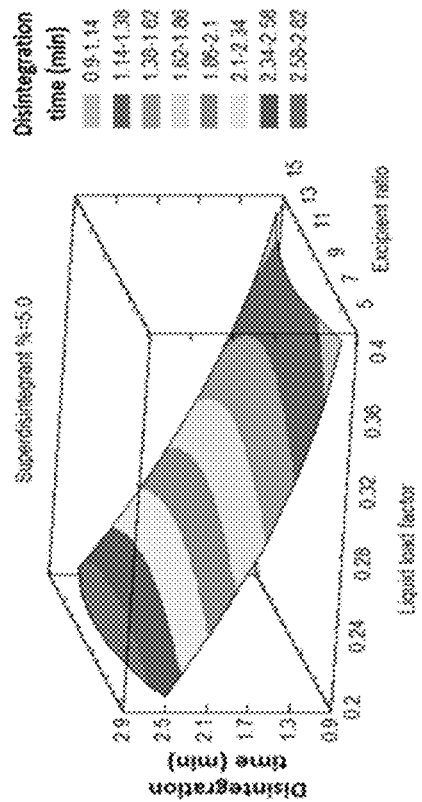

A similar finding was observed in the relationship between the disintegration time ($Y_2$) and the liquid load factor ($X_1$). FIG. 5c revealed that increasing the liquid load factor ($X_1$) in the LSTs showed an antagonistic effect on the tablet disintegration. The increase in $X_1$ from 0.2 to 0.4 was always accompanied by a decrease in the disintegration time of tablets. At the same level of both $X_2$ and $X_3$ and increasing the $X_1$ from 0.2 to 0.4, the disintegration time decreased from 2.54 to 1.13 min in LS-1 and LS-7, respectively and from 1.04 to 0.26 min in LS-3 and LS-4, respectively. This observation could be confirmed by the decrease of $Y_2$ from 2.32 to 1.12 min for LS-8 and LS-11, respectively. That, increasing Lf of the LSTs increasing the amount of liquid used and significantly increase the wetting characteristics and surface area of the drug and increasing the accessibility of the drug to be easily disintegrated from its LSTs, and this subsequently; accelerate its disintegration (K. El-Say et al., 2010).

It was evident that, when the percentage of $X_3$ and $X_1$ increased in the LSTs, the disintegration time of the prepared LSTs will significantly decrease with p values of 0.0001 and 0.0016 for $X_3$ and $X_1$, respectively as presented in Pareto chart (FIG. 4). The prediction equation (8) of disintegration time value is:

$$\text{Disintegration time } (Y_2) = 40.325 - 46.625X_1 + 0.302X_2 - 10.901X_3 + 23.791X_1^2 - 0.105X_1X_2 + 5.125X_1X_3 - 0.008X_2^2 - 0.018X_2X_3 + 0.768X_3^2 \quad \text{(Eq. 8)}$$

The disintegration time of formulations containing 6% of $X_3$ such as LS-2, LS-4, LS-3, and LS-5 had shorter disintegration times of 0.26, 0.57, 0.78 and 1.04 min, respectively. While the disintegration time of the formulations containing 4% of $X_3$ disintegrated is 6 min.

Effect of Independent Variables on the Dissolution Efficiency of TDL and DPX ($Y_3$ and $Y_4$)

Figures 6A, 6B:
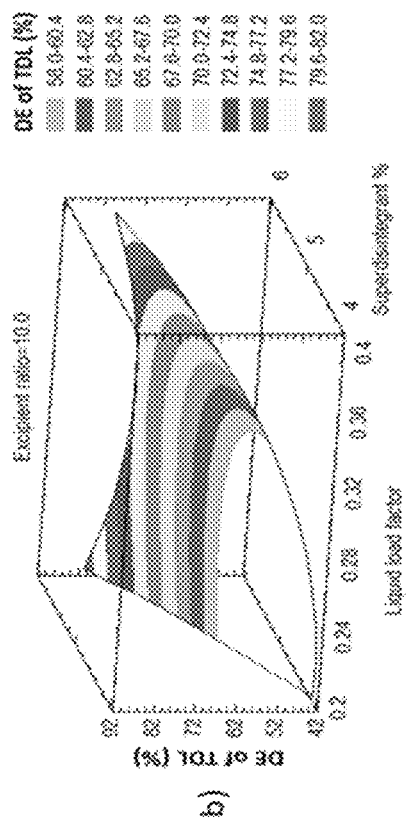
FIG. 6A-D. Response surface plots showing the effect of the independent variables on $Y_3$ and $Y_4$ (A-D).
Figure 6D:
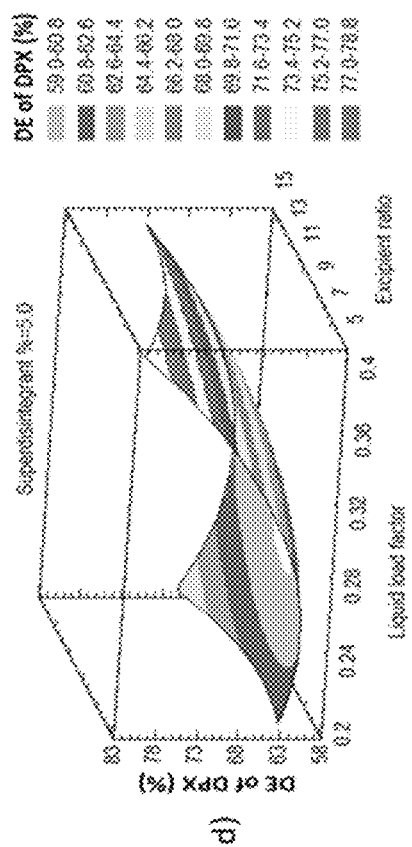

FIG. 6 revealed that the dissolution efficiency of TDL and DPX ($Y_3$ and $Y_4$) were significantly affected by both ($X_1$) and ($X_3$). There is a synergistic relationship between and liquid load factor ($X_1$) and superdisintegrant concentration ($X_3$), i.e. when the $X_1$ and $X_3$ increase the dissolution efficiency increases as well. As the $X_1$ increases from 0.2 to 0.4 at the same level of the other factors, $Y_3$ increases from 70.28 to 78.25% in LS-1 and LS-7, respectively and from 74.85 to 78.68% in LS-3 and LS-4, respectively. This trend can be confirmed by the increase in $Y_3$ from 70.91 to 82.18% in LS-8 and LS-10, respectively as $X_1$ increased from 0.2 to 0.4. When $X_3$ increases from 5 to 15 at the same level as other factors, $Y_3$ increases from 44.37 to 74.85% in LS-9 and LS-3, respectively. This trend can be confirmed by the increase in $Y_3$ from 55.25 to 87.87% in LS-6 and LS-2, respectively.

The same finding was observed for the dissolution efficiency of DPX ($Y_4$). Also, there is a significant synergistic effect of $X_3$ and $X_1$ on $Y_4$ as presented in FIGS. 5c&d. These significant effects can be found in LS-6 and LS-2 when increased from 54.19 to 91.81%, respectively by increasing $X_1$ from 5 to 15 at the same level of other factors. Other instances can be confirmed by increase the dissolution efficiency of DPX from 51.42 to 82.02% in LS-9 and LS-3, respectively.

Figure 6C:
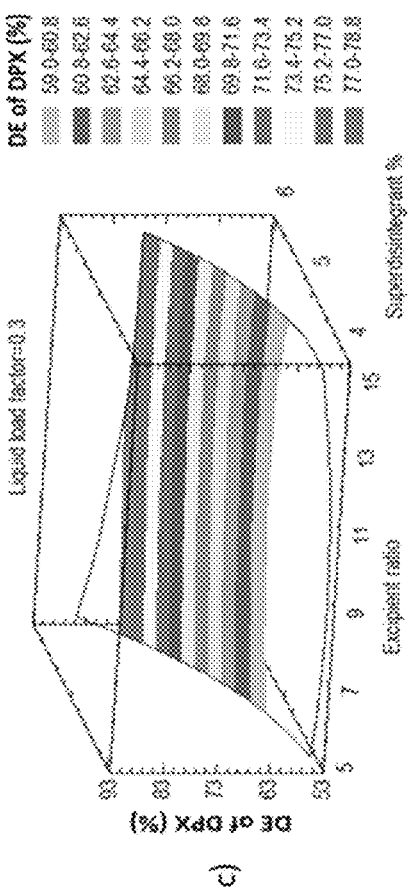

It was detected that both DE of TDL and DE of DPX are governed by the percentage of liquid load factor $X_1$ which had a significant synergistic effect on $Y_3$ and $Y_4$ with p values of 0.0233, and 0.0417, respectively (Table 4 and FIGS. 6c&d). Also, the superdisintegrant concentration ($X_3$) was found to have a significant synergistic effect on $Y_3$ and $Y_4$ with p-values of 0.0045 and 0.003, respectively. The model equations (9 and 10) to predict both responses are given below:

$$DE_{60} \text{ of } TDL\ (Y_3) = 6.73337 - 40.6675X_1 - 5.04273X_2 + 18.5641X_3 + 890.687X_1^2 - 1.647X_1X_2 - 80.665X_1X_3 + 0.308545X_2^2 - 0.21285X_2X_3 + 1.89712X_3^2 \quad \text{(Eq. 9)}$$

$$DE_{60} \text{ of } DPX\ (Y_4) = 93.8799 - 86.635X_1 + 2.18506X_2 - 28.633X_3 + 885.571X_1^2 - 6.158X_1X_2 - 63.605X_1X_3 + 0.0957783X_2^2 - 0.49905X_2X_3 + 6.52096X_3^2 \quad \text{(Eq. 10)}$$

The dissolution profiles of TDL and DPX from the LS formulations (FIG. 3), indicated that the initial and cumulative TDL and DPX release increased markedly in the formulations with the high percentage of $X_3$. An increase in $X_3$ from 4 to 6% at the same level of other factors, led to an increase in $Y_3$ from 44.37 to 87.871 for LS-9 and LS-2, respectively. The same finding was observed in LS-9 and LS-3 by increase $Y_3$ from 44.3 to 74.85 respectively. Also, this finding could be confirmed by the increase in the $Y_3$ from 51.63 to 79.42% for LS-12 and LS-5, respectively. The same formulations exposed a similar behavior regarding the $DE_{60}$ of DPX. This behavior can be explained by the release of surface-bound DPX from LSTs that could explain the initial rapid release phase. Moreover, it was found that there is a direct relationship between the polyplasdone % and the $DE_{60}$ of DPX. The $DE_{60}$ decreased from 91.8 to 55.2% in LS-2 and LS-6, respectively when the polyplasdone % decreased from 6 to 4% at the same level of $X_1$ and $X_2$. Also, $Y_4$ decreased from 82 to 51% in LS-3 and LS-9, respectively by decreasing $X_3$ from 6 to 4% at the same level of $X_1$ and $X_2$. Moreover, this finding could be confirmed by the decrease of $Y_3$ from 86.74 to 81.88% for LS-4 and LS-10, respectively due to the decrease in $X_3$ from 6 to 4% at the same level of $X_1$ and $X_2$. This finding may be due to the molecularly dispersed drug in the solvent used in the prepared LSTs which permits greater surface area in contact with the dissolution media that endorses the penetration of LSTs and improves the drug dissolution which consequently increases the $DE_{60}$ of both APIs.

Prediction of the Optimized Liquisolid Formulation

To compromise the investigated responses in an attempt to find the optimum combination of factors' levels, multiple response optimization was performed. Consequently, the desirability function over the specified design space of the obtained data was maximized Table 5 demonstrates the optimal calculated independent variables. The optimal combination of these factors ensured the desired hardness, disintegration time, and dissolution efficiency for both TDL and DPX. Furthermore, it was previously recognized that the higher dissolution efficiency exhibited by LSTs may also designate the improved oral bioavailability due to increase the wettability and the surface area of APIs accessible for dissolution (Fahmy and Kassem, 2008; Singh et al., 2012).

TABLE 5

Optimal calculated independent variables and observed, predicted and residual values for dependent variables.

| Independent variables | Optimum | Dependent variables | Predicted values | Observed values | Residuals |
|---|---|---|---|---|---|
| Liquid load factor | 0.2 | Hardness | 55.2 | 54.1 | 1.1 |
| Powder excipient ratio | 11.82 | Disintegration time | 2.7 | 2.8 | 0.1 |
| Superdisintegrant concentration | 5.11 | Dissolution efficiency for TDL at 60 min | 66.4 | 68.6 | −2.2 |
|  |  | Dissolution efficiency for DPX at 60 min | 74.5 | 77.2 | −2.7 |

In-Vivo Pharmacokinetics Evaluation on Human Volunteers

Figure 7B:
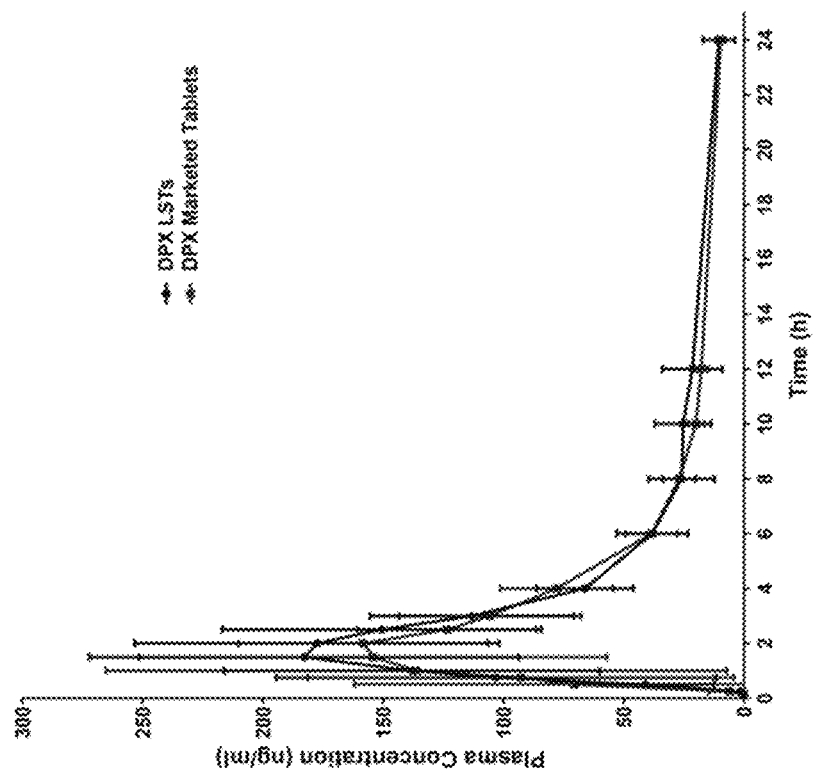
FIG. 7A-B. Plasma concentration time curve of A) TDL and B) DPX after a single oral dose.
Figure 7A:
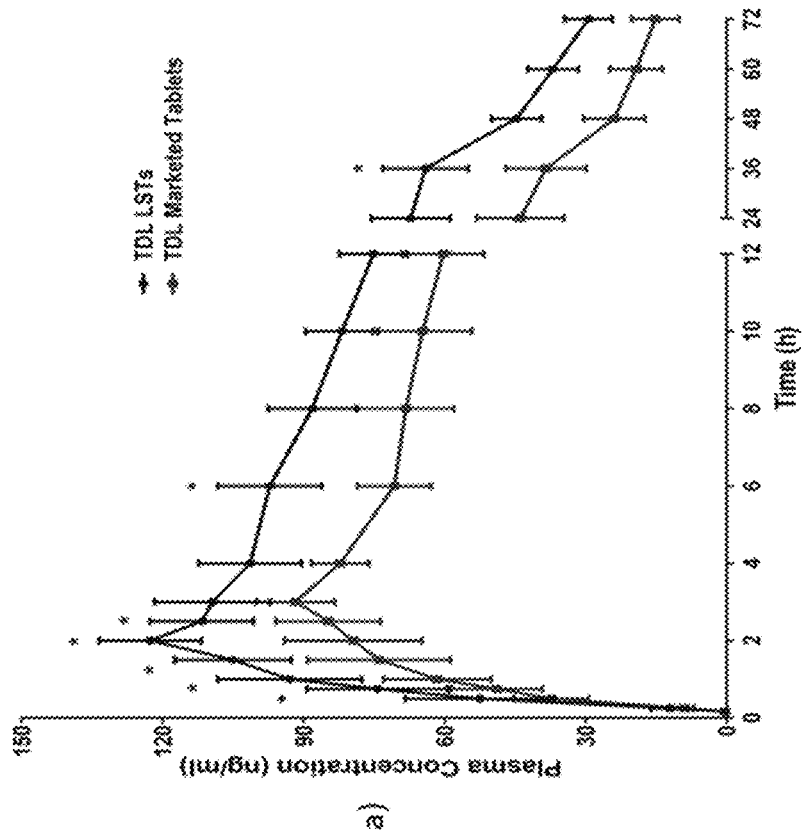

FIG. 7 displayed the plasma concentration-time curve profiles after oral administration of optimized LSTs compared to the marketed tablets. All the involved volunteers have fully completed the clinical study. The pharmacokinetic parameters of the clinical study are depicted in Table 6. The results indicated that the maximum plasma concentration ($C_{max}$) of TDL in LSTs was 122.61 ng/ml within 2 h ($T_{max}$), compared to the marketed tablets which reach to 91.72 ng/ml after 3 h. These findings indicated that the LST reached the maximum plasma concentration faster than the marketed tablet and consequently produced the rapid onset of therapeutic action. Amazingly, the optimized LST formulation achieved this $C_{max}$ of the marketed tablet after only 1 h which revealed that the LSTs formulation improved the rate and extent of TDL absorption compared to the marketed tablet. Also, LSTs showed higher AUC in comparison to the marketed tablets. The improved absorption of LSTs was probably due to the enhanced solubilization of the drugs and the high surface area available for absorption. The dissolved drug in LSTs can be directly absorbed, with a short time for the dissolution step which is considered the rate-limiting step for drug absorption in BCS Class II compounds. Improvement of the dissolution rate can lead to a significant increase in oral absorption and subsequently enhance oral bioavailability (Bakhtiari Kaboutaraki et al., 2015; Yasir et al., 2010). The relative bioavailability of TDL of LSTs was larger (170.6%) than that of the marketed tablet. Also, ANOVA of the data showed that there are significant differences (p<0.05) among the samples taken at 0.75, 1, 1.5, 2, 2.5, 6 and 36 h from the two groups of volunteers indicating the significant improvement achieved by the LSTs. Unpaired t-test with Welch's correction discovered that there is a significant difference between the $C_{max}$ and $AUC_{0-t}$ of both groups with p-values of 0.0198 and 0.0280, respectively. Regarding DPX, despite the higher relative bioavailability of DPX of the LST (117.05%) than of the marketed tablet, unpaired t-test with Welch's correction revealed that the LS formulation did not differ significantly from the marketed tablets concerning Cmax, $t_{max}$, and AUC(0-24) at P<0.05.

The pharmacokinetic evaluation revealed a significant improvement in the drug bioavailability after oral administration owing to the enhanced drug solubility and absorption. The pharmacokinetic parameters indicated that the maximum plasma concentration ($C_{max}$) of TDL in LSTs was 122.61 ng/ml within 2 h ($T_{max}$), compared to the marketed tablets which reach to 91.72 ng/ml after 3 h. Amazingly, the optimized LST formulation achieved this C. of the marketed tablet after only 1 h which revealed that LSTs formulation improved the rate and extent of TDL absorption. Also, the optimized formulation showed higher AUC in comparison to the marketed tablets. The improved absorption of LSTs was probably due to the enhanced solubilization of the drugs and the high surface area available for absorption. The dissolved APIs in the mixture of solvents used can be directly absorbed, with a short time for the dissolution step which is considered the rate-limiting step for drug absorption in BCS Class II compounds. Improvement of the dissolution rate leads to a significant increase in oral absorption and subsequently enhance oral bioavailability. The relative bioavailability of TDL of LSTs was larger (170.6%) than that of the marketed tablet. Also, ANOVA of the data showed that there are significant differences (p<0.05) among the samples taken at 0.75, 1, 1.5, 2, 2.5, 6 and 36 h from the two groups of volunteers indicating the significant improve-

TABLE 6

Pharmacokinetic parameters of TDL and DPX in the optimized Tadapox LSTs compared to TDL and DPX in the marketed tablets after oral administration of a single-dose to human volunteers (mean ± SD; n = 6)

| PK parameter | Unit | TDL | | DPX | |
| --- | --- | --- | --- | --- | --- |
| | | LSTs | Marketed Tablets | LSTs | Marketed Tablets |
| Lambda_z | 1/h | 0.104 ± 0.096 | 0.051 ± 0.034 | 0.065 ± 0.010 | 0.051 ± 0.006 |
| $t_{1/2}$ | H | 18.523 ± 22.737 | 17.544 ± 8.557 | 10.951 ± 1.879 | 11.683 ± 1.989 |
| Tmax | H | 2 ± 0 | 3 ± 0 | 1.667 ± 0.289 | 1.833 ± 0.289 |
| Cmax | ng/ml | 122.612* ± 10.876 | 91.719 ± 8.347 | 186.154 ± 83.741 | 171.063 ± 71.830 |
| AUC 0-t | ng/ml*h | 4484.953* ± 408.147 | 2994.611 ± 591.332 | 919.633 ± 397.978 | 794.699 ± 195.442 |
| AUC 0-inf | ng/ml*h | 5231.316 ± 1579.022 | 3066.42 ± 573.078 | 1096.416 ± 521.708 | 936.702 ± 170.519 |
| AUMC 0-inf | ng/ml*h^2 | 241586.7 ± 175386.7 | 97771.74 ± 20029.83 | 13201.782 ± 9197.529 | 10844.661 ± 983.277 |
| MRT 0-inf | H | 42.650 ± 17.812 | 31.878 ± 2.155 | 11.492 ± 3.034 | 11.915 ± 2.817 |
| Vz/F | (mg)/(ng/ml) | 0.021 ± 0.022 | 0.042 ± 0.023 | 0.504 ± 0.251 | 0.562 ± 0.185 |
| Cl/F | (mg)/(ng/ml)/h | 0.001 ± 0.0002 | 0.002 ± 0.0003 | 0.033 ± 0.018 | 0.033 ± 0.006 |

*Significant difference at p < 0.05 (unpaired t-test with Welch's correction). LSTs, liquisolid tablets; AUC, area under the time-concentration curve; Cmax, maximum plasma concentration; Tmax, time required to reach the Cmax; Lambda_z, elimination rate constant; MRT, mean residence time; Vz/F, Apparent volume of distribution during terminal phase; Cl/F, apparent total clearance of the drug from plasma after drug oral administration.

The optimized LS formulation containing 5 mg of TDL and 30 mg of DPX was compared with the marketed tablets with the same doses. The relative bioavailability of TDL was increased with rapid onset of action as reflected by the shorter time to reach the $t_{max}$. This result proves that the rapidity of onset of action, and the duration as well as the plasma drug concentration to be suitable for treatment of male sexual dysfunction.

CONCLUSIONS

From the obtained results, we concluded that BBD was successfully implemented in the optimization of the formulation factors to produce an optimized combined-dose of TDL and DPX liquisolid tablet with acceptable mechanical properties, short disintegration time, and good dissolution profile. The statistical analysis suggested the combination of the factor's level of 0.2 of the liquid load factor, 11.82 of the excipient ratio, and 5.11% of polyplasdone XL-10 in the preparation of the optimized formulation.

ment achieved by the LSTs. Unpaired t-test with Welch's correction discovered that there is a significant difference between the Cmax and AUC0-t of both groups with p-values of 0.0198 and 0.0280, respectively. Regarding DPX, despite the higher relative bioavailability of DPX of the LST (117.05%) than of the marketed tablet, unpaired t-test with Welch's correction revealed that the LS formulation did not differ significantly from the marketed tablets concerning Cmax, $t_{max}$, and AUC(0-24) at P<0.05.

Finally, the higher relative bioavailability exhibited by the optimized liquisolid formulation containing 5 mg of TDL and 30 mg of DPX with rapid onset of action is reflected by the shorter time to reach the $t_{max}$. This result reveals that the onset was rapid enough, and the duration and the concentration achieved a level suitable to overcome male sexual dysfunction. So, the developed combined-dose liquisolid formulation is a new approach in the treatment of male sexual dysfunction, particularly for diabetic patients.

Acknowledgment

This project was funded by the Deanship of Scientific Research (DSR) at King Abdulaziz University, Jeddah, under grant no. (RG-7-166-38). The inventors, therefore, acknowledge with thanks DSR for technical and financial support.

REFERENCES

Abourehab, M. A. S., Ahmed, O. A. A., Balata, G. F., Almalki, W. H., 2018. Self-assembled biodegradable polymeric micelles to improve dapoxetine delivery across the blood-brain barrier. Int. J. Nanomedicine 13, 3679-3687. doi.org/10.2147/IJN.S168148

Ahmed, O. A. A., 2018. Development and single dose clinical pharmacokinetics investigation of novel zein assisted-alpha lipoic acid nanoencapsulation of vardenafil. Sci. Rep. 8, 15802. doi.org/10.1038/541598-018-34235-8

Ahmed, T. A., El-Say, K. M., Hosny, K. M., Aljaeid, B. M., 2018. Development of optimized self-nanoemulsifying lyophilized tablets (SNELTs) to improve finasteride clinical pharmacokinetic behavior. Drug Dev. Ind. Pharm. 44, 652-661. doi.org/10.1080/03639045.2017.1405977

Ahuja, N., Katare, O. P., Singh, B., 2007. Studies on dissolution enhancement and mathematical modeling of drug release of a poorly water-soluble drug using water-soluble carriers. Eur. J. Pharm. Biopharm. 65, 26-38. doi.org/10.1016/j.ejpb.2006.07.007

Al-Subaie, M. M., Hosny, K. M., El-Say, K. M., Ahmed, T. A., Aljaeid, B. M., 2015. Utilization of nanotechnology to enhance percutaneous absorption of acyclovir in the treatment of herpes simplex viral infections. Int. J. Nanomedicine 10, 3973-3985. doi.org/10.2147/IJN.S83962

Aldawsari, H. M., Elfaky, M. A., Fahmy, U. A., Aljaeid, B. M., Alshareef, O. A., El-Say, K. M., 2018. Development of a fluvastatin-loaded self-nanoemulsifying system to maximize therapeutic efficacy in human colorectal carcinoma cells. J. Drug Deliv. Sci. Technol. 46, 7-13. doi.org/10.1016/j.jddst.2018.04.015

Althof, S. E., Abdo, C. H. N., Dean, J., Hackett, G., McCabe, M., McMahon, C. G., Rosen, R. C., Sadovsky, R., Waldinger, M., Becher, E., Broderick, G. A., Buvat, J., Goldstein, I., El-Meliegy, A. I., Giuliano, F., Hellstrom, W. J. G., Incrocci, L., Jannini, E. A., Park, K., Parish, S., Porst, H., Rowland, D., Segraves, R., Sharlip, I., Simonelli, C., Tan, H. M., 2010. International Society for Sexual Medicine's Guidelines for the Diagnosis and Treatment of Premature Ejaculation, Journal of Sexual Medicine. Elsevier Masson SAS. doi.org/10.1111/j.1743-6109.2010.01975.x Andersson, K. E., 2018. PDE5 inhibitors-pharmacology and clinical applications 20 years after sildenafil discovery. Br. J. Pharmacol. 175, 2554-2565. doi.org/10.1111/bph.14205

Avasthi, A., Biswas, P., 2004. Pharmacotherapy of sexual dysfunctions: current status. Indian J. Psychiatry 46, 213-220.

Badr-Eldin, S. M., Elkheshen, S. a, Ghorab, M. M., 2008. Inclusion complexes of tadalafil with natural and chemically modified beta-cyclodextrins. I: preparation and in-vitro evaluation. Eur. J. Pharm. Biopharm. 70, 819-27. doi.org/10.1016/j.ejpb.2008.06.024

Badr-Eldin, S. M., Elkheshen, S. A., Ghorab, M. M., 2017. Improving tadalafil dissolution via surfactant-enriched tablets approach: Statistical optimization, characterization, and pharmacokinetic assessment. J. Drug Deliv. Sci. Technol. 41, 197-205. doi.org/10.1016/j.jddst.2017.07.014

Bai, Y., Pu, C., Han, P., Li, J., Yuan, H., Tang, Y., Wang, X., Wei, Q., 2015. Selective Serotonin Reuptake Inhibitors Plus Phosphodiesterase-5 Inhibitors for Premature Ejaculation: A Systematic Review and Meta-analysis. Urology 86, 758-765. doi.org/10.1016/j.urology.2015.06.045

Baker, R. W., Lonsdale, H. S., 1974. Controlled release: mechanisms and release., in: Taquary, A. C., Lacey, R. E. (Eds), Controlled Release of Biological Active Agents. Plenum Press, New York. pp. 15-71.

Bakhtiari Kaboutaraki, H., Daeihamed, M., Haeri, A., Dadashzadeh, S., Arzani, G., 2015. Niosomal carriers enhance oral bioavailability of carvedilol: effects of bile salt-enriched vesicles and carrier surface charge  Int. J. Nanomedicine 4797. doi.org/10.2147/ijn.s84703

Bernal, N. P., Calpena, A. C., Mallandrich, M., Ruiz, A., Clares, B., 2014. Development, Physical-Chemical Stability, and Release Studies of Four Alcohol-Free Spironolactone Suspensions for Use in Pediatrics. Dissolution Technol. 21, 19-30. doi.org/10.14227/DT210114P19

Bushra, R., Shoaib, M. H., Ali, H., Zafar, F., Naeem, M. I., Aslam, N., Yousuf, R. I., 2014. Formulation design and Optimization of Aceclofenac Tablets (100 mg) using central composite design with response surface methodology. Lat. Am. J. Pharm. 33, 1009-1018.

Carr, R., 1965. Evaluating flow properties of solids. Chem. Eng. 72, 163.

Chella, N., Narra, N., Rao, T. R., 2014. Preparation and Characterization of Liquisolid Compacts for Improved Dissolution of Telmisartan. J. Drug Deliv. 692793, 10 pages.

Cooper, K., Martyn-St James, M., Kaltenthaler, E., Dickinson, K., Cantrell, A., Wylie, K., Frodsham, L., Hood, C., 2015. Behavioral Therapies for Management of Premature Ejaculation: A Systematic Review. Sex. Med. 3, 174-188. doi.org/10.1002/sm2.65

Corona, G., Rastrelli, G., Limoncin, E., Sforza, A., Jannini, E A, Maggi, M., 2015. Interplay Between Premature Ejaculation and Erectile Dysfunction: A Systematic Review and Meta-Analysis. J. Sex. Med. 12, 2291-2300. doi.org/10.1111/jsm.13041

De Hong, C., Ren, L. L., Yu, H., Qiang, W., 2014. The role of dapoxetine hydrochloride on-demand for the treatment of men with premature ejaculation. Sci. Rep. 4, 7269. doi.org/10.1038/srep07269

Desai, S., Singh, P., Simonelli, A., Higuchi, W., 1966. Investigation of factors influencing release of solid drug dispersed in inert matrices III. Quantitative studies involving the polyethylene plastic matrix. J. Pharm. Sci. 55, 1230-1234.

Dresser, M. J., Desai, D., Gidwani, S., Seftel, A. D., Modi, N. B., 2006. Dapoxetine, a novel treatment for premature ejaculation, does not have pharmacokinetic interactions with phosphodiesterase-5 inhibitors. Int. J. Impot. Res. 18, 104-110. doi.org/10.1038/sj.ijir.3901420

El-Say, K., Samy, A., Fetouh, M., 2010. Formulation and evaluation of rofecoxib liquisolid tablets. Int. J. Pharm. Sci. Rev. Res. 3, 135-142. doi.org/10.3797/scipharm.0912-23

El-Say, K. M., Ahmed, O. A. A., Aldawsari, H. M., Badr-Eldin, S. M., 2019. Influence of different variables on the dissolution behavior of carvedilol from liquisolid compacts using response surface methodolgy. Dig. J. Nanomater. Biostructures 14, 879-894.

El-Say, K. M., Ahmed, T. A. A., Ahmed, O. A. A., Hosny, K. M., Abd-Allah, F. I., 2017. Self-Nanoemulsifying Lyophilized Tablets for Flash Oral Transmucosal Delivery of Vitamin K: Development and Clinical Evaluation. J. Pharm. Sci. 106, 2447-2456. doi.org/10.1016/j.xphs.2017.01.001

El-Say, K. M., El-Sawy, H. S., 2017. Polymeric nanoparticles: Promising platform for drug delivery. Int. J. Pharm. 528, 675-691. doi.org/10.1016/j.ijpharm.2017.06.052

El-Say, K. M., Samy, A. M., Fetouh, M. I., 2010. Optimization of Rofecoxib Liquisolid Tablets using Box-Behnken Design and Desirability Function. J. Pharm. Res. 3, 2388-2392.

El-Sayyad, N. M. E.-M., Badawi, A., Abdullah, M. E., Abdelmalak, N. S., 2017. Dissolution enhancement of leflunomide incorporating self emulsifying drug delivery systems and liquisolid concepts. Bull. Fac. Pharmacy, Cairo Univ. 55, 53-62. doi.org/10.1016/j.bfopcu.2017.02.001

Elkordy, A. A., Tan, X. N., Essa, E. A., 2013. Spironolactone release from liquisolid formulations prepared with Capryol™ 90, Solutol® HS-15 and Kollicoat® SR 30 D as non-volatile liquid vehicles. Eur. J. Pharm. Biopharm. 83, 203-223. doi.org/10.1016/j.ejpb.2012.08.004

Erion, M. D., van Poelje, P. D., MacKenna, D. A., Colby, T. J., Montag, A. C., Fujitaki, J. M., Linemeyer, D. L., Bullough, D. A., 2005. Liver-Targeted Drug Delivery Using HepDirect Prodrugs. J. Pharmacol. Exp. Ther. 312, 554-560. doi.org/10.1124/jpet.104.075903

Fahmy, R., Kassem, M., 2008. Enhancement of famotidine dissolution rate through liquisolid tablets formulation: In vitro and in vivo evaluation. Eur. J. Pharm. Biopharm. 69, 993-1003. doi.org/10.1016/j.ejpb.2008.02.017

Gao, J., Zhang, X., Su, P., Liu, J., Xia, L., Yang, J., Shi, K., Tang, D., Hao, Z., Zhou, J., Liang, C., 2013. Prevalence and factors associated with the complaint of premature ejaculation and the four premature ejaculation syndromes: A large observational study in China. J. Sex. Med. 10, 1874-1881. doi.org/10.1111/jsm.12180

Hausner, N. H., 1967. Flow Properties of some Pharmaceutical Powders. Int. J. Powder Met. 3, 7-11.

Higuchi, T., 1963. Mechanism of sustained-action medication. Theoretical analysis of rate of release of solid drugs dispersed in solid matrices. J. Pharm. Sci. 52, 1145-1149.

Hixson, A. W., Crowell, J. H., 1931. Dependence of Reaction Velocity upon surface and Agitation. Ind. Eng. Chem. 23, 923-931. doi.org/10.1021/ie50260a018

Hu, L., Zhang, H., Song, W., Gu, D., Hu, Q., 2012. Investigation of inclusion complex of cilnidipine with hydroxypropylβ-cyclodextrin. Carbohydr. Polym. 90, 1719-1724.

Javadzadeh, Y., Musaalrezaei, L., Nokhodchi, A., 2008. Liquisolid technique as a new approach to sustain propranolol hydrochloride release from tablet matrices. Int. J. Pharm. 362, 102-8. doi.org/10.1016/j.ijpharm.2008.06.022

Keck, C. M., Müller, R. H., 2006. Drug nanocrystals of poorly soluble drugs produced by high pressure homogenisation. Eur. J. Pharm. Biopharm. 62, 3-16. doi.org/10.1016/j.ejpb.2005.05.009

Kornblum, S. S., Stoopak, S. B., 1973. A New Tablet Disintegrating Agent: Cross-Linked Polyvinylpyrrolidone. J. Pharm. Sci. 62, 43-49. doi.org/10.1002/JPS.2600620107

Korsmeyer, R., Gurny, R., Doelker, E., Buri, P., Peppas, N., 1983. Mechanisms of potassium chloride release from compressed, hydrophilic, polymeric matrices: effect of entrapped air. J. Pharm. Sci. 15, 1189-1191. doi.org/10.1016/0378-5173(83)90064-9

Langenbucher, F., 1972. Linearization of dissolution rate curves by the Weibull distribution. J. Pharm. Pharmacol. 24, 979-81.

Lee, W. K., Lee, S. H., Cho, S. T., Lee, Y. S., Oh, C. Y., Yoo, C., Cho, J. S., Lee, S. K., Yang, D. Y., 2013. Comparison between on-demand dosing of dapoxetine alone and dapoxetine plus mirodenafil in patients with lifelong premature ejaculation: Prospective, randomized, double-blind, placebo-controlled, multicenter study. J. Sex. Med. 10, 2832-2841. doi.org/10.1111/jsm.12287

Li, J., Liu, D., Wu, J., Fan, X., Dong, Q., 2018. Dapoxetine for the treatment of premature ejaculation: a meta-analysis of randomized controlled trials with trial sequential analysis. Ann. Saudi Med. 38, 366-375. doi.org/10.5144/0256-4947.2018.366

Malavige, L. S., Jayaratne, S. D., Kathriarachchi, S. T., Sivayogan, S., Fernando, D. J., Levy, J. C., 2008. Erectile dysfunction among men with diabetes is strongly associated with premature ejaculation and reduced libido. J. Sex. Med. 5, 2125-2134. doi.org/10.1111/j.1743-6109.2008.00907.x Mateescu, C., Popescu, A. M., Radu, G. L., Onisei, T., Raducanu, A. E., 2017. Spectroscopic and spectrometric methods used for the screening of certain herbal food supplements suspected of adulteration. Adv. Pharm. Bull. 7, 251-259. doi.org/10.15171/apb.2017.030

Mcmahon, C. G., Giuliano, F., Dean, J., Hellstrom, W. J. G., Bull, S., Tesfaye, F., Sharma, O., Rivas, D. A., Aquilina, J. W., 2013. Efficacy and safety of dapoxetine in men with premature ejaculation and concomitant erectile dysfunction treated with a phosphodiesterase type 5 inhibitor: Randomized, placebo-controlled, phase III study. J. Sex. Med. 10, 2312-2325. doi.org/10.1111/jsm.12236

Meyer, K., Zimmermann, I., 2004. Effect of glidants in binary powder mixtures. Powder Technol. 139, 40-54. doi.org/10.1016/j.powtec.2003.09.007

Nokhodchi, A., Javadzadeh, Y., Siahi-Shadbad, M. R., Barzegar-Jalali, M., 2005. The effect of type and concentration of vehicles on the dissolution rate of a poorly soluble drug (indomethacin) from liquisolid compacts. J. Pharm. Pharm. Sci. 8, 18-25.

Pandya, P., 2010. Solubility enhancement techniques Why??? 5, 1-36.

Papadopoulou, V., Kosmidis, K., Vlachou, M., Macheras, P., 2006. On the use of the Weibull function for the discernment of drug release mechanisms. Int. J. Pharm. 309, 44-50. doi.org/10.1016/j.ijpharm.2005.10.044

Park, H. J., Park, N. C., Kim, T. N., Baek, S. R., Lee, K. M., Choe, S., 2017. Discontinuation of Dapoxetine Treatment in Patients With Premature Ejaculation: A 2-Year Prospective Observational Study. Sex. Med. 5, e99-e105. doi.org/10.1016/j.esxm.2017.02.003

Patel, D. S., Pipaliya, R. M., Surti, N., 2015. Liquisolid Tablets for Dissolution Enhancement of a Hypolipidemic Drug. Indian J. Pharm. Sci. 77, 290-298. doi.org/10.4103/0250-474X.159618

Patel, M., Shah, A., Patel, N. M., Patel, M. R., Patel, K. R., 2011. Nano Suspension: a Novel Approch for Drug Delivery System. J. Pharm. Sci. Biosci. Res. 1, 1-10.

Pisansky, T. M., Pugh, S. L., Greenberg, R. E., Pervez, N., Reed, D. R., Rosenthal, S. A., Mowat, R. B., Raben, A., Buyyounouski, M. K., Kachnic, L. A., Bruner, D. W., 2014. Tadalafil for Prevention of Erectile Dysfunction After Radiotherapy for Prostate Cancer. Jama 311, 1300. doi.org/10.1001/jama.2014.2626

Ramezani, M. A., Ahmadi, K., Ghaemmaghami, A., Marzabadi, E. A., Pardakhti, F., 2015. Epidemiology of sexual dysfunction in iran: A systematic review and meta-analysis. Int. J. Prey. Med. 2015-May. doi.org/10.4103/2008-7802.157472

Rastrelli, G., Cipriani, S., Corona, G., Vignozzi, L., Maggi, M., 2019. Clinical characteristics of men complaining of premature ejaculation together with erectile dysfunction: a cross-sectional study. Andrology 7, 163-171. doi.org/10.1111/andr.12579

Saeedi, M., Akbari, J., Morteza-Semnani, K., Enayati-Fard, R., Sar-Reshteh-Dar, S., Soleymani, A., 2011. Enhancement of dissolution rate of indomethacin using liquisolid compacts. Iran. J. Pharm. Res. 10, 25-34. doi.org/10.1016/j.farmac.2004.09.005

Sangkum, P., Badr, R., Serefoglu, E. C., Hellstrom, W. J. G., 2013. Dapoxetine and the treatment of premature ejaculation. Transl. Androl. Urol. 2, 301-311. doi.org/10.3978/j.issn.2223-4683.2013.12.01

Sanjay, P. D., Deepak, M., Bhanudas, S. R., 2013. Liquisolid technology: Technique for formulation with enhanced bioavailability. WORLD J. Pharm. Pharm. Sci. 3, 368-387.

Sanka, K., Poienti, S., Mohd, A., Diwan, P., 2014. Improved oral delivery of clonazepam through liquisolid powder compact formulations: In-vitro and ex-vivo characterization. Powder Technol. 256, 336-344.

Satriyasa, B. K., 2017. Tadalafil as New Treatment in Erectile Dysfunction: A Review. Bali Med. J. 6, 56. doi.org/10.15562/bmj.v6i1.370

Serefoglu, E. C., Yaman, O., Cayan, S., Asci, R., Orhan, I., Usta, M. F., Ekmekcioglu, O., Kendirci, M., Semerci, B., Kadioglu, A., 2011. Prevalence of the Complaint of Ejaculating Prematurely and the Four Premature Ejaculation Syndromes: Results from the Turkish Society of Andrology Sexual Health Survey. J. Sex. Med. 8, 540-548. doi.org/10.1111/j.1743-6109.2010.02095.x Singh, S. K., Srinivasan, K. K., Gowthamarajan, K., Prakash, D., Gaikwad, N. B., Singare, D. S., 2012. Influence of formulation parameters on dissolution rate enhancement of glyburide using liquisolid technique. Drug Dev. Ind. Pharm. 38, 961-970. doi.org/10.3109/03639045.2011.634810

Sousa Lobo, J. M., Costa, P., 2001. Modeling and comparison of dissolution profiles. Eur. J. Pharm. Sci. 13, 123-133.

Staniforth, J. N., Aulton, M. E., 2007. Powder flow, in: Aulton, M. E. (Ed.), Aulton Pharmaceutics: The Design and Manufacture of Medicines. Churchill Living stone Elservier, London, pp. 168-180.

Tayel, S. a., Soliman, L I., Louis, D., 2008. Improvement of dissolution properties of Carbamazepine through application of the liquisolid tablet technique. Eur J Pharm Biopharm 69, 342-347. doi.org/10.1016/j.ejpb.2007.09.003 The United States Pharmacopeia, T. N. F., 2005. USP 28/NF 23. US Pharmacopoeial Convention Inc., Rockville, Md., USA.

The United States Pharmacopeial Convention, 2011. Uniformity of Dosage Units. Stage 6 Harmonization (905).

Tsai, W.-K., Chiang, P.-K., Lu, C.-C., Jiann, B.-P., 2019. The Comorbidity Between Premature Ejaculation and Erectile Dysfunction-A Cross-Sectional Internet Survey. Sex. Med. 1-8. doi.org/10.1016/j.esxm.2019.06.014

Wagner, J. G., 1969. Interpretation of percent dissolved-time plots derived from in vitro testing of conventional tablets and capsules. J. Pharm. Sci. 58, 1253-7.

Walke, P., Pawar, A., Sonawane, D., Bhamber, R., 2011. Liquisolid: A novel technique to enhance solubility and dissolution rate of BCS class II Pharmaceuticals. J. Pharm. Res. 4, 4011-4014.

Yasir, M., Asif, M., Kumar, A., Aggarval, A., Pharmacy, D. J. C., 2010. BCS journal1.pdf. Int. J. PharmTech Res. 2, 1681-1690.

Yen, S.-Y., Chen, C.-R., Lee, M.-T., Chen, L.-C., 1997. Investigation of Dissolution Enhancement of Nifedipine by Deposition on Superdisintegrants. Drug Dev. Ind. Pharm. 23, 313-317. doi.org/10.3109/03639049709149809

Zhang, K., Xu, B., Liu, D.-F., Wang, X.-F., Zhu, J.-C., Jin, J., Jiang, H., 2014. Medical management of erectile dysfunction in aging males: is it too late to treat? Asian J. Androl. 16, 153-6. doi.org/10.4103/1008-682X.122580

Zimmermann, I., Eber, M., Meyer, K., 2004. Nanomaterials as Flow Regulators in Dry Powders. Zeitschrift fur Phys. Chemie 218, 51-102. doi.org/10.1524/zpch.218.1.51.25388

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A liquisolid tablet formulation, comprising
a microcrystalline cellulose carrier;
a silica coating;
a crosslinked polyvinylpyrrolidone (PVP) superdisintegrant;
tadalafil dissolved in a first solvent comprising polyethylene glycol (PEG) 200; and
dapoxetine dissolved in a second solvent comprising caprylocaproyl macrogol-8 glycerides,
wherein the liquid load factor of the formulation is 0.2-0.4.

2. The formulation of claim 1, wherein the liquid load factor is 0.2.

3. The formulation of claim 1, wherein the carrier to coating ratio is 11-13.

4. The formulation of claim 1, wherein the concentration of superdisintegrant is 4-6%.

5. The formulation of claim 1, wherein the ratio of PEG 200 to caprylocaproyl macrogol-8 glycerides is 1:1.

6. The formulation of claim 1, wherein the dose of tadalafil is 2.5-5 mg and the dose of dapoxetine is 15-30 mg.

7. A method of preparing a liquisolid tablet formulation, comprising
dissolving tadalafil in a solvent comprising PEG 200;
dissolving dapoxetine in a solvent comprising caprylocaproyl macrogol-8 glycerides;
mixing the dissolved tadalafil and the dissolved dapoxetine to form a combined solution;
adding a microcrystalline cellulose carrier, a crosslinked polyvinylpyrrolidone (PVP) superdisintegrant, and silica coating to the combined solution to form a dry mixture; and
compressing the dry mixture to form a liquisolid tablet.

8. The method of claim 7, wherein the liquid load factor of the liquisolid tablet is 0.2.

9. The method of claim 7, wherein the carrier to coating ratio in the liquisolid tablet is 11-13.

10. The method of claim 7, wherein the concentration of superdisintegrant in the liquisolid tablet is 4-6%.

11. The method of claim 7, wherein the ratio of PEG 200 to caprylocaproyl macrogol-8 glycerides in the combined solution is 1:1.

12. The method of claim 7, wherein the dose of tadalafil is 2.5-5 mg and the dose of dapoxetine in the liquisolid tablet is 15-30 mg.

13. A method of treating male sexual dysfunction in a subject in need thereof, comprising administering a therapeutically effective amount of the formulation of claim 1 to the subject.

* * * * *